(12) United States Patent
Dong et al.

(10) Patent No.: US 9,925,346 B2
(45) Date of Patent: Mar. 27, 2018

(54) SYSTEMS AND METHODS FOR VENTILATION WITH UNKNOWN EXHALATION FLOW

(71) Applicant: Covidien LP, Boulder, CO (US)

(72) Inventors: Nancy F. Dong, Carlsbad, CA (US); Gabriel Sanchez, Valley Center, CA (US)

(73) Assignee: Covidien LP, Boulder, CO (US)

( * ) Notice: Subject to any disclaimer, the term of this patent is extended or adjusted under 35 U.S.C. 154(b) by 437 days.

(21) Appl. No.: 14/600,261

(22) Filed: Jan. 20, 2015

(65) Prior Publication Data

US 2016/0206837 A1 Jul. 21, 2016

(51) Int. Cl.
*A61M 16/00* (2006.01)
*A61M 16/04* (2006.01)
*A61M 16/06* (2006.01)
*A61M 16/20* (2006.01)

(52) U.S. Cl.
CPC ........ *A61M 16/0069* (2014.02); *A61M 16/00* (2013.01); *A61M 16/0003* (2014.02); *A61M 16/0051* (2013.01); *A61M 16/04* (2013.01); *A61M 16/06* (2013.01); *A61M 16/20* (2013.01); *A61M 16/0063* (2014.02); *A61M 2016/003* (2013.01); *A61M 2016/0027* (2013.01); *A61M 2205/14* (2013.01); *A61M 2205/18* (2013.01); *A61M 2205/3334* (2013.01); *A61M 2205/52* (2013.01)

(58) Field of Classification Search
CPC .............. A61M 16/0069; A61M 16/00; A61M 16/0051; A61M 16/04; A61M 16/06; A61M 16/20; A61M 16/0003; A61M 16/0063; A61M 2205/18; A61M 2205/3334; A61M 2205/52
See application file for complete search history.

(56) References Cited

U.S. PATENT DOCUMENTS

| | | | |
|---|---|---|---|
| 3,584,621 A | 6/1971 | Bird et al. |
| 3,586,021 A | 6/1971 | McGuinness |
| 3,633,576 A | 1/1972 | Gorsuch |
| 3,662,751 A | 5/1972 | Barkalow et al. |
| 3,664,370 A | 5/1972 | Warnow |
| 3,669,108 A | 6/1972 | Sundblom et al. |
| 3,695,263 A | 10/1972 | Kipling |
| 3,741,208 A | 6/1973 | Jonsson et al. |
| 3,753,436 A | 8/1973 | Bird et al. |
| 3,756,229 A | 9/1973 | Ollivier |
| 3,768,468 A | 10/1973 | Cox |
| 3,789,837 A | 2/1974 | Philips et al. |
| 3,827,433 A | 8/1974 | Shannon |

(Continued)

FOREIGN PATENT DOCUMENTS

EP 2509669 A1 10/2012
WO 2003055552 7/2003

OTHER PUBLICATIONS

PCT International Search Report and Written Opinion in International Application PCT/US2016/014131, dated Apr. 8, 2016, 11 pgs.

(Continued)

*Primary Examiner* — Steven Douglas

(57) ABSTRACT

Systems and methods for ventilation that allows the patient to trigger or initiate the delivery of a breath are provided. Further, systems and methods for triggering ventilation when exhalation flow is unknown or unreliable by the ventilator are provided.

20 Claims, 3 Drawing Sheets

(56) References Cited

U.S. PATENT DOCUMENTS

| | | |
|---|---|---|
| 3,834,382 A | 9/1974 | Lederman et al. |
| 3,869,771 A | 3/1975 | Bollinger |
| 3,889,669 A | 6/1975 | Weigl |
| 3,889,670 A | 6/1975 | Loveland et al. |
| 3,896,800 A | 7/1975 | Cibulka |
| 3,903,881 A | 9/1975 | Weigl |
| 3,905,362 A | 9/1975 | Eyrick et al. |
| 3,908,987 A | 9/1975 | Boehringer |
| 3,910,261 A | 10/1975 | Ragsdale et al. |
| 3,923,056 A | 12/1975 | Bingmann et al. |
| 3,961,627 A | 6/1976 | Ernst et al. |
| 3,976,052 A | 8/1976 | Junginger et al. |
| 3,976,065 A | 8/1976 | Durkan |
| 3,981,301 A | 9/1976 | Warnow et al. |
| 4,003,377 A | 1/1977 | Dahl |
| 4,020,834 A | 5/1977 | Bird |
| 4,029,120 A | 6/1977 | Christianson |
| 4,044,763 A | 8/1977 | Bird |
| 4,050,458 A | 9/1977 | Friend |
| 4,057,059 A | 11/1977 | Reid, Jr. et al. |
| 4,060,078 A | 11/1977 | Bird |
| 4,082,093 A | 4/1978 | Fry et al. |
| 4,121,578 A | 10/1978 | Torzala |
| 4,155,357 A | 5/1979 | Dahl |
| 4,164,219 A | 8/1979 | Bird |
| 4,197,843 A | 4/1980 | Bird |
| 4,197,856 A | 4/1980 | Northrop |
| 4,206,754 A | 6/1980 | Cox et al. |
| 4,211,221 A | 7/1980 | Schwanbom et al. |
| 4,211,239 A | 7/1980 | Raemer et al. |
| 4,227,523 A | 10/1980 | Warnow et al. |
| 4,232,666 A | 11/1980 | Savelli et al. |
| 4,245,633 A | 1/1981 | Erceg |
| 4,265,237 A | 5/1981 | Schwanbom et al. |
| 4,267,827 A | 5/1981 | Racher et al. |
| 4,275,722 A | 6/1981 | Sorensen |
| 4,281,651 A | 8/1981 | Cox |
| 4,285,340 A | 8/1981 | Gezari et al. |
| 4,320,754 A | 3/1982 | Watson et al. |
| 4,323,064 A | 4/1982 | Hoenig et al. |
| 4,340,044 A | 7/1982 | Levy et al. |
| 4,351,328 A | 9/1982 | Bodai |
| 4,351,329 A | 9/1982 | Ellestad et al. |
| 4,351,344 A | 9/1982 | Stenzler |
| 4,401,115 A | 8/1983 | Monnier |
| 4,417,573 A | 11/1983 | De Vries |
| 4,436,090 A | 3/1984 | Darling |
| 4,457,304 A | 7/1984 | Molnar et al. |
| 4,459,982 A | 7/1984 | Fry |
| 4,459,983 A | 7/1984 | Beyreuther et al. |
| 4,462,397 A | 7/1984 | Suzuki |
| 4,502,481 A | 3/1985 | Christian |
| 4,527,557 A | 7/1985 | DeVries et al. |
| 4,539,984 A | 9/1985 | Kiszel et al. |
| 4,554,916 A | 11/1985 | Watt |
| 4,558,710 A | 12/1985 | Eichler |
| 4,566,450 A | 1/1986 | Brossman, Jr. |
| 4,596,246 A | 6/1986 | Lyall |
| 4,598,706 A | 7/1986 | Darowski et al. |
| 4,611,591 A | 9/1986 | Inui et al. |
| 4,612,928 A | 9/1986 | Tiep et al. |
| 4,622,976 A | 11/1986 | Timpe et al. |
| 4,640,277 A | 2/1987 | Meyer et al. |
| 4,648,407 A | 3/1987 | Sackner |
| 4,651,731 A | 3/1987 | Vicenzi et al. |
| 4,752,089 A | 6/1988 | Carter |
| 4,757,824 A | 7/1988 | Chaumet |
| 4,766,894 A | 8/1988 | Legrand et al. |
| 4,796,618 A | 1/1989 | Garraffa |
| 4,813,409 A | 3/1989 | Ismach |
| 4,821,709 A | 4/1989 | Jensen |
| 4,877,023 A | 10/1989 | Zalkin |
| 4,889,116 A | 12/1989 | Taube |
| 4,921,642 A | 5/1990 | LaTorraca |
| 4,924,862 A | 5/1990 | Levinson |
| 4,954,799 A | 9/1990 | Kumar |
| 4,981,295 A | 1/1991 | Belman et al. |
| 4,982,735 A | 1/1991 | Yagata et al. |
| 5,002,050 A | 3/1991 | McGinnis |
| 5,007,420 A | 4/1991 | Bird |
| 5,016,626 A | 5/1991 | Jones |
| 5,057,822 A | 10/1991 | Hoffman |
| 5,063,925 A | 11/1991 | Frank et al. |
| 5,065,746 A | 11/1991 | Steen |
| 5,067,487 A | 11/1991 | Bauman |
| 5,072,737 A | 12/1991 | Goulding |
| 5,099,837 A | 3/1992 | Russel, Sr. et al. |
| 5,150,291 A | 9/1992 | Cummings et al. |
| 5,154,167 A | 10/1992 | Hepburn |
| 5,158,569 A | 10/1992 | Strickland et al. |
| 5,161,525 A | 11/1992 | Kimm et al. |
| 5,165,397 A | 11/1992 | Arp |
| 5,165,398 A | 11/1992 | Bird |
| 5,222,491 A | 6/1993 | Thomas |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,667 A | 4/1994 | McGrail et al. |
| 5,301,921 A | 4/1994 | Kumar |
| 5,303,698 A | 4/1994 | Tobia et al. |
| 5,315,989 A | 5/1994 | Tobia |
| 5,316,009 A | 5/1994 | Yamada |
| 5,318,487 A | 6/1994 | Golen et al. |
| 5,319,540 A | 6/1994 | Isaza et al. |
| 5,323,772 A | 6/1994 | Linden et al. |
| 5,325,861 A | 7/1994 | Goulding |
| 5,333,606 A | 8/1994 | Schneider et al. |
| 5,335,651 A | 8/1994 | Foster et al. |
| 5,335,654 A | 8/1994 | Rapoport |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,373,842 A | 12/1994 | Olsson et al. |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,404,871 A | 4/1995 | Goodman et al. |
| 5,407,174 A | 4/1995 | Kumar |
| 5,413,110 A | 5/1995 | Cummings et al. |
| 5,429,123 A | 7/1995 | Shaffer et al. |
| 5,433,193 A | 7/1995 | Sanders et al. |
| 5,438,980 A | 8/1995 | Phillips |
| 5,443,075 A | 8/1995 | Holscher |
| 5,458,137 A | 10/1995 | Axe et al. |
| 5,479,920 A | 1/1996 | Piper et al. |
| 5,487,383 A | 1/1996 | Levinson |
| 5,494,028 A | 2/1996 | DeVries et al. |
| 5,507,282 A | 4/1996 | Younes |
| 5,509,406 A | 4/1996 | Kock et al. |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,535,738 A | 7/1996 | Estes et al. |
| 5,540,220 A | 7/1996 | Gropper et al. |
| 5,542,415 A | 8/1996 | Brady |
| 5,544,674 A | 8/1996 | Kelly |
| 5,549,106 A | 8/1996 | Gruenke et al. |
| 5,549,655 A | 8/1996 | Erickson |
| 5,551,419 A | 9/1996 | Froehlich et al. |
| 5,564,416 A | 10/1996 | Jones |
| 5,575,283 A | 11/1996 | Sjoestrand |
| 5,582,163 A | 12/1996 | Bonassa |
| 5,596,984 A | 1/1997 | O'Mahoney et al. |
| 5,603,315 A | 2/1997 | Sasso, Jr. |
| 5,606,968 A | 3/1997 | Mang |
| 5,615,669 A | 4/1997 | Olsson et al. |
| 5,630,411 A | 5/1997 | Holscher |

(56) References Cited

U.S. PATENT DOCUMENTS

| | | |
|---|---|---|
| 5,632,269 A | 5/1997 | Zdrojkowski |
| 5,632,270 A | 5/1997 | O'Mahony et al. |
| 5,645,048 A | 7/1997 | Brodsky et al. |
| 5,645,053 A | 7/1997 | Remmers et al. |
| 5,647,345 A | 7/1997 | Saul |
| 5,647,351 A | 7/1997 | Weismann et al. |
| 5,651,360 A | 7/1997 | Tobia |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,694,926 A | 12/1997 | DeVries et al. |
| 5,706,799 A | 1/1998 | Imai et al. |
| 5,715,812 A | 2/1998 | Deighan et al. |
| 5,720,277 A | 2/1998 | Olsson et al. |
| 5,727,562 A | 3/1998 | Beck |
| 5,730,122 A | 3/1998 | Lurie |
| 5,735,267 A | 4/1998 | Tobia |
| 5,738,090 A | 4/1998 | Lachmann et al. |
| 5,740,796 A | 4/1998 | Skog |
| 5,752,509 A | 5/1998 | Lachmann et al. |
| 5,762,480 A | 6/1998 | Adahan |
| 5,769,072 A | 6/1998 | Olsson et al. |
| 5,771,884 A | 6/1998 | Yarnall et al. |
| 5,791,339 A | 8/1998 | Winter |
| 5,794,615 A | 8/1998 | Estes |
| 5,794,986 A | 8/1998 | Gansel et al. |
| 5,803,066 A | 9/1998 | Rapoport et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,865,173 A | 2/1999 | Froehlich |
| 5,868,133 A | 2/1999 | DeVries et al. |
| 5,881,717 A | 3/1999 | Isaza |
| 5,881,723 A | 3/1999 | Wallace et al. |
| 5,884,623 A | 3/1999 | Winter |
| 5,906,204 A | 5/1999 | Beran et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,381 A | 6/1999 | Nord |
| 5,915,382 A | 6/1999 | Power |
| 5,918,597 A | 7/1999 | Jones et al. |
| 5,921,238 A | 7/1999 | Bourdon |
| 5,927,274 A | 7/1999 | Servidio et al. |
| 5,931,162 A | 8/1999 | Christian |
| 5,934,274 A | 8/1999 | Merrick et al. |
| 5,970,975 A | 10/1999 | Estes et al. |
| 5,975,081 A | 11/1999 | Hood et al. |
| 5,983,891 A | 11/1999 | Fukunaga |
| 6,000,396 A | 12/1999 | Melker et al. |
| 6,003,513 A | 12/1999 | Readey et al. |
| 6,010,459 A | 1/2000 | Silkoff et al. |
| 6,024,089 A | 2/2000 | Wallace et al. |
| 6,029,664 A | 2/2000 | Zdrojkowski et al. |
| 6,029,667 A | 2/2000 | Lurie |
| 6,041,780 A | 3/2000 | Richard et al. |
| 6,042,550 A | 3/2000 | Haryadi et al. |
| 6,044,841 A | 4/2000 | Verdun et al. |
| 6,047,860 A | 4/2000 | Sanders |
| 6,066,101 A | 5/2000 | Johnson et al. |
| 6,067,984 A | 5/2000 | Piper |
| 6,076,519 A | 6/2000 | Johnson |
| 6,076,523 A | 6/2000 | Jones et al. |
| 6,095,139 A | 8/2000 | Psaros |
| 6,095,140 A | 8/2000 | Poon et al. |
| 6,102,038 A | 8/2000 | DeVries |
| 6,105,575 A | 8/2000 | Estes et al. |
| 6,116,240 A | 9/2000 | Merrick et al. |
| 6,116,464 A | 9/2000 | Sanders |
| 6,123,073 A | 9/2000 | Schlawin et al. |
| 6,123,674 A | 9/2000 | Rich |
| 6,135,106 A | 10/2000 | Dirks et al. |
| 6,138,675 A | 10/2000 | Berthon-Jones |
| 6,142,150 A | 11/2000 | O'Mahoney |
| 6,148,814 A | 11/2000 | Clemmer et al. |
| 6,152,132 A | 11/2000 | Psaros |
| 6,158,432 A | 12/2000 | Biondi et al. |
| 6,158,433 A | 12/2000 | Ong et al. |
| 6,161,539 A | 12/2000 | Winter |
| 6,192,885 B1 | 2/2001 | Jalde |
| 6,200,271 B1 | 3/2001 | Kuck et al. |
| 6,210,342 B1 | 4/2001 | Kuck et al. |
| 6,213,119 B1 | 4/2001 | Brydon et al. |
| 6,217,524 B1 | 4/2001 | Orr et al. |
| 6,220,244 B1 | 4/2001 | McLaughlin |
| 6,220,245 B1 | 4/2001 | Takabayashi et al. |
| 6,230,708 B1 | 5/2001 | Radko |
| 6,238,351 B1 | 5/2001 | Orr et al. |
| 6,241,681 B1 | 6/2001 | Haryadi et al. |
| 6,258,038 B1 | 7/2001 | Haryadi et al. |
| 6,269,812 B1 | 8/2001 | Wallace et al. |
| 6,273,444 B1 | 8/2001 | Power |
| 6,283,119 B1 | 9/2001 | Bourdon |
| 6,305,373 B1 | 10/2001 | Wallace et al. |
| 6,305,374 B1 | 10/2001 | Zdrojkowski et al. |
| 6,306,098 B1 | 10/2001 | Orr et al. |
| 6,318,365 B1 | 11/2001 | Vogele et al. |
| 6,321,748 B1 | 11/2001 | O'Mahoney |
| 6,325,785 B1 | 12/2001 | Babkes et al. |
| 6,345,619 B1 | 2/2002 | Finn |
| 6,357,438 B1 | 3/2002 | Hansen |
| 6,360,745 B1 | 3/2002 | Wallace et al. |
| 6,369,838 B1 | 4/2002 | Wallace et al. |
| 6,412,483 B1 | 7/2002 | Jones et al. |
| 6,427,692 B1 | 8/2002 | Hoglund |
| 6,439,229 B1 | 8/2002 | Du et al. |
| 6,443,154 B1 | 9/2002 | Jalde et al. |
| 6,450,163 B1 | 9/2002 | Blacker et al. |
| 6,450,968 B1 | 9/2002 | Wallen et al. |
| 6,467,477 B1 | 10/2002 | Frank et al. |
| 6,467,478 B1 | 10/2002 | Merrick et al. |
| 6,510,846 B1 | 1/2003 | O'Rourke |
| 6,512,938 B2 | 1/2003 | Claure et al. |
| 6,526,970 B2 | 3/2003 | DeVries et al. |
| 6,532,957 B2 | 3/2003 | Berthon-Jones |
| 6,532,960 B1 | 3/2003 | Yurko |
| 6,537,228 B1 | 3/2003 | Lambert |
| 6,539,940 B2 | 4/2003 | Zdrojkowski et al. |
| 6,546,930 B1 | 4/2003 | Emerson et al. |
| 6,553,991 B1 | 4/2003 | Isaza |
| 6,557,553 B1 | 5/2003 | Borrello |
| 6,560,991 B1 | 5/2003 | Kotliar |
| 6,564,798 B1 | 5/2003 | Jalde |
| 6,568,387 B2 | 5/2003 | Davenport et al. |
| 6,571,795 B2 | 6/2003 | Bourdon |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,595,212 B1 | 7/2003 | Arnott |
| 6,601,583 B2 | 8/2003 | Pessala et al. |
| 6,609,517 B1 | 8/2003 | Estes et al. |
| 6,622,725 B1 | 9/2003 | Fisher et al. |
| 6,622,726 B1 | 9/2003 | Du |
| 6,626,175 B2 | 9/2003 | Jafari et al. |
| 6,640,806 B2 | 11/2003 | Yurko |
| 6,644,310 B1 | 11/2003 | Delache et al. |
| 6,659,100 B2 | 12/2003 | O'Rourke |
| 6,662,032 B1 | 12/2003 | Gavish et al. |
| 6,668,824 B1 | 12/2003 | Isaza et al. |
| 6,671,529 B2 | 12/2003 | Claure et al. |
| 6,675,801 B2 | 1/2004 | Wallace et al. |
| 6,679,258 B1 | 1/2004 | Strom |
| 6,688,307 B2 | 2/2004 | Berthon-Jones |
| 6,694,978 B1 | 2/2004 | Bennarsten |
| 6,705,314 B1 | 3/2004 | O'Dea |
| 6,718,974 B1 | 4/2004 | Moberg |
| 6,722,360 B2 | 4/2004 | Doshi |
| 6,725,447 B1 | 4/2004 | Gilman et al. |
| 6,739,337 B2 | 5/2004 | Isaza |

(56) References Cited

U.S. PATENT DOCUMENTS

| | | |
|---|---|---|
| 6,752,151 B2 | 6/2004 | Hill |
| 6,758,216 B1 | 7/2004 | Berthon-Jones et al. |
| 6,761,167 B1 | 7/2004 | Nadjafizadeh et al. |
| 6,761,168 B1 | 7/2004 | Nadjafizadeh et al. |
| 6,776,159 B2 | 8/2004 | Pelerossi et al. |
| 6,782,888 B1 | 8/2004 | Friberg et al. |
| 6,786,216 B2 | 9/2004 | O'Rourke |
| 6,810,876 B2 | 11/2004 | Berthon-Jones |
| 6,814,074 B1 | 11/2004 | Nadjafizadeh et al. |
| 6,823,866 B2 | 11/2004 | Jafari et al. |
| 6,848,444 B2 | 2/2005 | Smith et al. |
| 6,854,462 B2 | 2/2005 | Berthon-Jones et al. |
| 6,863,068 B2 | 3/2005 | Jamison et al. |
| 6,863,656 B2 | 3/2005 | Lurie |
| 6,866,040 B1 | 3/2005 | Bourdon |
| 6,877,511 B2 | 4/2005 | DeVries et al. |
| 6,899,103 B1 | 5/2005 | Hood et al. |
| 6,915,803 B2 | 7/2005 | Berthon-Jones et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,948,497 B2 | 9/2005 | Zdrojkowski et al. |
| 6,960,854 B2 | 11/2005 | Nadjafizadeh et al. |
| 6,962,155 B1 | 11/2005 | Sinderby |
| 6,986,347 B2 | 1/2006 | Hickle |
| 6,986,349 B2 | 1/2006 | Lurie |
| 6,988,498 B2 | 1/2006 | Berthon-Jones et al. |
| 6,990,980 B2 | 1/2006 | Richey, II |
| 7,000,612 B2 | 2/2006 | Jafari et al. |
| 7,008,380 B1 | 3/2006 | Rees et al. |
| 7,011,091 B2 | 3/2006 | Hill et al. |
| 7,011,092 B2 | 3/2006 | McCombs et al. |
| 7,032,589 B2 | 4/2006 | Kerechanin, II et al. |
| 7,036,504 B2 | 5/2006 | Wallace et al. |
| 7,040,318 B2 | 5/2006 | Däscher et al. |
| 7,056,334 B2 | 6/2006 | Lennox |
| 7,066,175 B2 | 6/2006 | Hamilton et al. |
| 7,066,177 B2 | 6/2006 | Pittaway et al. |
| 7,070,570 B2 | 7/2006 | Sanderson et al. |
| 7,077,131 B2 | 7/2006 | Hansen |
| 7,077,132 B2 | 7/2006 | Berthon-Jones |
| 7,080,646 B2 | 7/2006 | Wiesmann et al. |
| RE39,225 E | 8/2006 | Isaza et al. |
| 7,087,027 B2 | 8/2006 | Page |
| 7,089,932 B2 | 8/2006 | Dodds |
| 7,096,866 B2 | 8/2006 | Be'eri et al. |
| 7,100,607 B2 | 9/2006 | Zdrojkowski et al. |
| 7,100,609 B2 | 9/2006 | Berthon-Jones et al. |
| 7,104,962 B2 | 9/2006 | Lomask et al. |
| 7,117,438 B2 | 10/2006 | Wallace et al. |
| 7,121,277 B2 | 10/2006 | Ström |
| 7,122,010 B2 | 10/2006 | Böhm et al. |
| 7,128,069 B2 | 10/2006 | Farrugia et al. |
| 7,137,389 B2 | 11/2006 | Berthon-Jones |
| 7,152,598 B2 | 12/2006 | Morris et al. |
| 7,152,604 B2 | 12/2006 | Hickle et al. |
| 7,156,095 B2 | 1/2007 | Melker et al. |
| 7,204,251 B2 | 4/2007 | Lurie |
| 7,211,049 B2 | 5/2007 | Bradley et al. |
| 7,219,666 B2 | 5/2007 | Friberg et al. |
| 7,246,618 B2 | 7/2007 | Habashi |
| 7,255,103 B2 | 8/2007 | Bassin |
| 7,267,122 B2 | 9/2007 | Hill |
| 7,267,652 B2 | 9/2007 | Coyle et al. |
| 7,270,126 B2 | 9/2007 | Wallace et al. |
| 7,270,128 B2 | 9/2007 | Berthon-Jones et al. |
| 7,275,540 B2 | 10/2007 | Bolam et al. |
| 7,276,031 B2 | 10/2007 | Norman et al. |
| 7,278,962 B2 | 10/2007 | Lönneker Lammers |
| 7,290,544 B1 | 11/2007 | Särelä et al. |
| 7,296,573 B2 | 11/2007 | Estes et al. |
| 7,308,894 B2 | 12/2007 | Hickle |
| 7,311,668 B2 | 12/2007 | Lurie |
| 7,320,321 B2 | 1/2008 | Pranger et al. |
| 7,353,824 B1 | 4/2008 | Forsyth et al. |
| 7,369,757 B2 | 5/2008 | Farbarik |
| 7,370,650 B2 | 5/2008 | Nadjafizadeh et al. |
| 7,390,304 B2 | 6/2008 | Chen et al. |
| 7,392,806 B2 | 7/2008 | Yuen et al. |
| 7,428,902 B2 | 9/2008 | Du et al. |
| 7,460,959 B2 | 12/2008 | Jafari |
| 7,465,275 B2 | 12/2008 | Stenqvist |
| 7,467,012 B1 | 12/2008 | Park et al. |
| 7,472,702 B2 | 1/2009 | Beck et al. |
| 7,478,634 B2 | 1/2009 | Jam |
| 7,481,222 B2 | 1/2009 | Reissmann |
| 7,487,773 B2 | 2/2009 | Li |
| 7,487,774 B2 | 2/2009 | Acker |
| 7,487,778 B2 | 2/2009 | Freitag |
| 7,527,058 B2 | 5/2009 | Wright et al. |
| RE40,814 E | 6/2009 | Van Brunt et al. |
| 7,547,285 B2 | 6/2009 | Kline |
| 7,552,731 B2 | 6/2009 | Jorczak et al. |
| 7,556,038 B2 | 7/2009 | Kirby et al. |
| 7,556,041 B2 | 7/2009 | Madsen |
| 7,562,657 B2 | 7/2009 | Blanch et al. |
| 7,574,368 B2 | 8/2009 | Pawlikowski et al. |
| 7,581,708 B2 | 9/2009 | Newkirk |
| 7,588,033 B2 | 9/2009 | Wondka |
| 7,617,824 B2 | 11/2009 | Doyle |
| 7,621,270 B2 | 11/2009 | Morris et al. |
| 7,628,151 B2 | 12/2009 | Bassin |
| 7,644,713 B2 | 1/2010 | Berthon-Jones |
| 7,654,802 B2 | 2/2010 | Crawford, Jr. et al. |
| 7,672,720 B2 | 3/2010 | Heath |
| 7,682,312 B2 | 3/2010 | Lurie |
| 7,686,019 B2 | 3/2010 | Weiss et al. |
| 7,694,677 B2 | 4/2010 | Tang |
| 7,708,015 B2 | 5/2010 | Seeger et al. |
| 7,717,113 B2 | 5/2010 | Andrieux |
| 7,717,858 B2 | 5/2010 | Massad |
| 7,721,736 B2 | 5/2010 | Urias et al. |
| 7,722,546 B2 | 5/2010 | Madaus et al. |
| D618,356 S | 6/2010 | Ross |
| 7,730,884 B2 | 6/2010 | Sato et al. |
| 7,735,486 B2 | 6/2010 | Payne |
| 7,735,492 B2 | 6/2010 | Doshi et al. |
| 7,775,207 B2 | 8/2010 | Jaffe et al. |
| 7,784,461 B2 | 8/2010 | Figueiredo et al. |
| 7,793,656 B2 | 9/2010 | Johnson |
| 7,798,145 B2 | 9/2010 | Weismann et al. |
| 7,798,148 B2 | 9/2010 | Doshi et al. |
| 7,802,571 B2 | 9/2010 | Tehrani |
| 7,806,120 B2 | 10/2010 | Loomas et al. |
| 7,810,496 B2 | 10/2010 | Estes et al. |
| 7,810,497 B2 | 10/2010 | Pittman et al. |
| 7,810,498 B1 | 10/2010 | Patterson |
| 7,823,588 B2 | 11/2010 | Hansen |
| 7,841,347 B2 | 11/2010 | Sonnenschein et al. |
| 7,849,854 B2 | 12/2010 | DeVries et al. |
| 7,850,619 B2 | 12/2010 | Gavish et al. |
| 7,855,716 B2 | 12/2010 | McCreary et al. |
| 7,866,318 B2 | 1/2011 | Bassin |
| D632,796 S | 2/2011 | Ross et al. |
| D632,797 S | 2/2011 | Ross et al. |
| 7,886,739 B2 | 2/2011 | Soliman et al. |
| 7,891,354 B2 | 2/2011 | Farbarik |
| 7,893,560 B2 | 2/2011 | Carter |
| 7,909,034 B2 | 3/2011 | Sinderby et al. |
| D638,852 S | 5/2011 | Skidmore et al. |
| 7,938,114 B2 | 5/2011 | Matthews et al. |
| 7,963,283 B2 | 6/2011 | Sinderby |
| 7,970,475 B2 | 6/2011 | Tehrani et al. |
| 7,971,589 B2 | 7/2011 | Mashak et al. |
| 7,984,712 B2 | 7/2011 | Soliman et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 7,992,564 B2 | 8/2011 | Doshi et al. |
| 7,997,271 B2 | 8/2011 | Hickle et al. |
| 8,001,967 B2 | 8/2011 | Wallace et al. |
| D645,158 S | 9/2011 | Sanchez et al. |
| 8,011,363 B2 | 9/2011 | Johnson |
| 8,011,364 B2 | 9/2011 | Johnson |

(56) References Cited

U.S. PATENT DOCUMENTS

| | | |
|---|---|---|
| 8,011,366 B2 | 9/2011 | Knepper |
| 8,015,974 B2 | 9/2011 | Christopher et al. |
| 8,020,558 B2 | 9/2011 | Christopher et al. |
| 8,021,308 B2 | 9/2011 | Carlson et al. |
| 8,021,309 B2 | 9/2011 | Zilberg |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| D692,556 S | 10/2013 | Winter |
| D693,001 S | 11/2013 | Winter |
| D701,601 S | 3/2014 | Winter |
| 8,792,949 B2 | 7/2014 | Baker, Jr. |
| 8,844,526 B2 | 9/2014 | Jafari et al. |
| D731,048 S | 6/2015 | Winter |
| D731,049 S | 6/2015 | Winter |
| D731,065 S | 6/2015 | Winter |
| D736,905 S | 8/2015 | Winter |
| D744,095 S | 11/2015 | Winter |
| 2001/0004893 A1 | 6/2001 | Biondi et al. |
| 2002/0017301 A1 | 2/2002 | Lundin |
| 2002/0026941 A1 | 3/2002 | Biondi et al. |
| 2002/0042564 A1 | 4/2002 | Cooper et al. |
| 2002/0042565 A1 | 4/2002 | Cooper et al. |
| 2002/0117173 A1 | 8/2002 | Lynn et al. |
| 2002/0144681 A1 | 10/2002 | Cewers et al. |
| 2003/0029453 A1 | 2/2003 | Smith et al. |
| 2003/0140925 A1 | 7/2003 | Sapienza et al. |
| 2003/0168066 A1 | 9/2003 | Sallvin |
| 2003/0172929 A1 | 9/2003 | Muellner |
| 2003/0225339 A1 | 12/2003 | Orr et al. |
| 2004/0149282 A1 | 8/2004 | Hickle |
| 2004/0244804 A1 | 12/2004 | Olsen et al. |
| 2005/0034724 A1 | 2/2005 | O'Dea |
| 2005/0034727 A1 | 2/2005 | Shusterman et al. |
| 2005/0039748 A1 | 2/2005 | Andrieux |
| 2005/0085865 A1 | 4/2005 | Tehrani |
| 2005/0085867 A1 | 4/2005 | Tehrani et al. |
| 2005/0085868 A1 | 4/2005 | Tehrani et al. |
| 2005/0113668 A1 | 5/2005 | Srinivasan |
| 2005/0139212 A1 | 6/2005 | Bourdon |
| 2005/0166928 A1 | 8/2005 | Jiang |
| 2005/0247311 A1 | 11/2005 | Vacchiano et al. |
| 2005/0279358 A1 | 12/2005 | Richey, II |
| 2006/0021618 A1 | 2/2006 | Berthon-Jones et al. |
| 2006/0122662 A1 | 6/2006 | Tehrani et al. |
| 2006/0142815 A1 | 6/2006 | Tehrani et al. |
| 2006/0196507 A1 | 9/2006 | Bradley |
| 2006/0196508 A1 | 9/2006 | Chalvignac |
| 2006/0241708 A1 | 10/2006 | Boute |
| 2006/0249153 A1 | 11/2006 | DeVries et al. |
| 2006/0264762 A1 | 11/2006 | Starr |
| 2006/0272637 A1 | 12/2006 | Johnson |
| 2006/0283451 A1 | 12/2006 | Albertelli |
| 2007/0017515 A1 | 1/2007 | Wallace et al. |
| 2007/0017518 A1 | 1/2007 | Farrugia et al. |
| 2007/0017522 A1 | 1/2007 | Be-Eri et al. |
| 2007/0017523 A1 | 1/2007 | Be-Eri et al. |
| 2007/0056588 A1 | 3/2007 | Hayek |
| 2007/0062532 A1 | 3/2007 | Choncholas |
| 2007/0062533 A1 | 3/2007 | Choncholas et al. |
| 2007/0068528 A1 | 3/2007 | Bohm et al. |
| 2007/0077200 A1 | 4/2007 | Baker |
| 2007/0089741 A1 | 4/2007 | Bohm et al. |
| 2007/0123792 A1 | 5/2007 | Kline |
| 2007/0125377 A1 | 6/2007 | Heinonen et al. |
| 2007/0129646 A1 | 6/2007 | Heinonen et al. |
| 2007/0157931 A1 | 7/2007 | Parker et al. |
| 2007/0181122 A1 | 8/2007 | Mulier |
| 2007/0227537 A1 | 10/2007 | Bemister et al. |
| 2007/0272241 A1 | 11/2007 | Sanborn et al. |
| 2007/0283958 A1 | 12/2007 | Naghavi |
| 2007/0284361 A1 | 12/2007 | Nadjafizadeh et al. |
| 2008/0000475 A1 | 1/2008 | Hill |
| 2008/0011296 A1 | 1/2008 | Schatzl |
| 2008/0021379 A1 | 1/2008 | Hickle |
| 2008/0033304 A1 | 2/2008 | Dalal et al. |
| 2008/0041383 A1 | 2/2008 | Matthews et al. |
| 2008/0045845 A1 | 2/2008 | Pfeiffer et al. |
| 2008/0053441 A1 | 3/2008 | Gottlib et al. |
| 2008/0060656 A1 | 3/2008 | Isaza |
| 2008/0072896 A1 | 3/2008 | Setzer et al. |
| 2008/0072901 A1 | 3/2008 | Habashi |
| 2008/0072902 A1 | 3/2008 | Setzer et al. |
| 2008/0072904 A1 | 3/2008 | Becker et al. |
| 2008/0078390 A1 | 4/2008 | Milne et al. |
| 2008/0078395 A1 | 4/2008 | Ho et al. |
| 2008/0083644 A1 | 4/2008 | Janbakhsh et al. |
| 2008/0091117 A1 | 4/2008 | Choncholas et al. |
| 2008/0092894 A1 | 4/2008 | Nicolazzi et al. |
| 2008/0097234 A1 | 4/2008 | Nicolazzi et al. |
| 2008/0110460 A1 | 5/2008 | Elaz et al. |
| 2008/0110461 A1 | 5/2008 | Mulqueeny et al. |
| 2008/0110462 A1 | 5/2008 | Chekal et al. |
| 2008/0135044 A1 | 6/2008 | Freitag et al. |
| 2008/0163872 A1 | 7/2008 | Negele et al. |
| 2008/0168990 A1 | 7/2008 | Cooke et al. |
| 2008/0178874 A1 | 7/2008 | Doshi et al. |
| 2008/0183057 A1 | 7/2008 | Taube |
| 2008/0183239 A1 | 7/2008 | Tehrani et al. |
| 2008/0183240 A1 | 7/2008 | Tehrani et al. |
| 2008/0188903 A1 | 8/2008 | Tehrani et al. |
| 2008/0196720 A1 | 8/2008 | Kollmeyer et al. |
| 2008/0200775 A1 | 8/2008 | Lynn |
| 2008/0202525 A1 | 8/2008 | Mitton et al. |
| 2008/0202528 A1 | 8/2008 | Carter et al. |
| 2008/0208281 A1 | 8/2008 | Tehrani et al. |
| 2008/0221470 A1 | 9/2008 | Sather et al. |
| 2008/0223361 A1 | 9/2008 | Nieuwstad |
| 2008/0230061 A1 | 9/2008 | Tham |
| 2008/0230062 A1 | 9/2008 | Tham |
| 2008/0236582 A1 | 10/2008 | Tehrani |
| 2008/0283060 A1 | 11/2008 | Bassin |
| 2008/0295837 A1 | 12/2008 | McCormick et al. |
| 2008/0312519 A1 | 12/2008 | Maschke |
| 2008/0314385 A1 | 12/2008 | Brunner et al. |
| 2009/0007914 A1 | 1/2009 | Bateman |
| 2009/0013999 A1 | 1/2009 | Bassin |
| 2009/0020119 A1 | 1/2009 | Eger et al. |
| 2009/0038617 A1 | 2/2009 | Berthon-Jones et al. |
| 2009/0071478 A1 | 3/2009 | Kalfon |
| 2009/0090359 A1 | 4/2009 | Daviet et al. |
| 2009/0095297 A1 | 4/2009 | Hallett |
| 2009/0099621 A1 | 4/2009 | Lin et al. |
| 2009/0107982 A1 | 4/2009 | McGhin et al. |
| 2009/0114223 A1 | 5/2009 | Bonassa |
| 2009/0137919 A1 | 5/2009 | Bar-Lavie et al. |
| 2009/0139522 A1 | 6/2009 | Thomson et al. |
| 2009/0145441 A1 | 6/2009 | Doshi et al. |
| 2009/0159082 A1 | 6/2009 | Eger |
| 2009/0165795 A1 | 7/2009 | Nadjafizadeh et al. |
| 2009/0165798 A1 | 7/2009 | Cong et al. |
| 2009/0171176 A1 | 7/2009 | Andersohn |
| 2009/0183739 A1 | 7/2009 | Wondka |
| 2009/0194109 A1 | 8/2009 | Doshi et al. |
| 2009/0205660 A1 | 8/2009 | Thomson et al. |
| 2009/0205661 A1 | 8/2009 | Stephenson et al. |
| 2009/0205663 A1 | 8/2009 | Vandine et al. |
| 2009/0210032 A1 | 8/2009 | Beiski et al. |

(56) References Cited

U.S. PATENT DOCUMENTS

| | | |
|---|---|---|
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. et al. |
| 2009/0241958 A1 | 10/2009 | Baker, Jr. |
| 2009/0241962 A1 | 10/2009 | Jafari et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0250058 A1 | 10/2009 | Lastow et al. |
| 2009/0260625 A1 | 10/2009 | Wondka |
| 2009/0266360 A1 | 10/2009 | Acker et al. |
| 2009/0272381 A1 | 11/2009 | Dellaca et al. |
| 2009/0277448 A1 | 11/2009 | Ahlmén et al. |
| 2009/0293872 A1 | 12/2009 | Bocke |
| 2009/0293877 A1 | 12/2009 | Blanch et al. |
| 2009/0299155 A1 | 12/2009 | Yang et al. |
| 2009/0301486 A1 | 12/2009 | Masic |
| 2009/0301487 A1 | 12/2009 | Masic |
| 2009/0301488 A1 | 12/2009 | Sun |
| 2009/0301490 A1 | 12/2009 | Masic |
| 2009/0301491 A1 | 12/2009 | Masic et al. |
| 2009/0301492 A1 | 12/2009 | Wysocki et al. |
| 2009/0308393 A1 | 12/2009 | Luceros |
| 2009/0308394 A1 | 12/2009 | Levi |
| 2009/0308398 A1 | 12/2009 | Ferdinand et al. |
| 2009/0314297 A1 | 12/2009 | Mathews |
| 2010/0011307 A1 | 1/2010 | Desfossez et al. |
| 2010/0016694 A1 | 1/2010 | Martin et al. |
| 2010/0018531 A1 | 1/2010 | Bassin |
| 2010/0024818 A1 | 2/2010 | Stenzler et al. |
| 2010/0024820 A1 | 2/2010 | Bourdon |
| 2010/0031443 A1 | 2/2010 | Georgiev et al. |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0076322 A1 | 3/2010 | Shrivastav et al. |
| 2010/0076323 A1 | 3/2010 | Shrivastav et al. |
| 2010/0078017 A1 | 4/2010 | Andrieux et al. |
| 2010/0078018 A1 | 4/2010 | Heinonen et al. |
| 2010/0078024 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0089396 A1 | 4/2010 | Richard et al. |
| 2010/0094366 A1 | 4/2010 | McCarthy |
| 2010/0101575 A1 | 4/2010 | Fedorko et al. |
| 2010/0108066 A1 | 5/2010 | Martin et al. |
| 2010/0108070 A1 | 5/2010 | Kwok |
| 2010/0114218 A1 | 5/2010 | Heath |
| 2010/0116270 A1 | 5/2010 | Edwards et al. |
| 2010/0125227 A1 | 5/2010 | Bird |
| 2010/0139660 A1 | 6/2010 | Adahan |
| 2010/0147302 A1 | 6/2010 | Selvarajan et al. |
| 2010/0147303 A1 | 6/2010 | Jafari et al. |
| 2010/0148458 A1 | 6/2010 | Ross et al. |
| 2010/0175695 A1 | 7/2010 | Jamison |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0241159 A1 | 9/2010 | Li |
| 2010/0242961 A1 | 9/2010 | Mougel et al. |
| 2010/0249549 A1 | 9/2010 | Baker, Jr. et al. |
| 2010/0249584 A1 | 9/2010 | Albertelli |
| 2010/0252037 A1 | 10/2010 | Wondka et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252046 A1 | 10/2010 | Dahlström et al. |
| 2010/0258124 A1 | 10/2010 | Madaus et al. |
| 2010/0275920 A1 | 11/2010 | Tham et al. |
| 2010/0275921 A1 | 11/2010 | Schindhelm et al. |
| 2010/0282259 A1 | 11/2010 | Figueiredo et al. |
| 2010/0288283 A1 | 11/2010 | Campbell et al. |
| 2010/0300445 A1 | 12/2010 | Chatburn et al. |
| 2010/0300446 A1 | 12/2010 | Nicolazzi et al. |
| 2010/0307507 A1 | 12/2010 | Li et al. |
| 2010/0319691 A1 | 12/2010 | Lurie et al. |
| 2010/0326442 A1 | 12/2010 | Hamilton et al. |
| 2010/0326447 A1 | 12/2010 | Loomas et al. |
| 2010/0331877 A1 | 12/2010 | Li et al. |
| 2011/0005530 A1 | 1/2011 | Doshi et al. |
| 2011/0009762 A1 | 1/2011 | Eichler et al. |
| 2011/0011400 A1 | 1/2011 | Gentner et al. |
| 2011/0017214 A1 | 1/2011 | Tehrani |
| 2011/0023875 A1 | 2/2011 | Ledwith |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0030686 A1 | 2/2011 | Wilkinson et al. |
| 2011/0036352 A1 | 2/2011 | Estes et al. |
| 2011/0041849 A1 | 2/2011 | Chen et al. |
| 2011/0041850 A1 | 2/2011 | Vandine et al. |
| 2011/0061650 A1 | 3/2011 | Heesch |
| 2011/0073112 A1 | 3/2011 | DiBlasi et al. |
| 2011/0088697 A1 | 4/2011 | DeVries et al. |
| 2011/0092841 A1 | 4/2011 | Bassin |
| 2011/0100365 A1 | 5/2011 | Wedler et al. |
| 2011/0108041 A1 | 5/2011 | Sather et al. |
| 2011/0112424 A1 | 5/2011 | Kesselman et al. |
| 2011/0112425 A1 | 5/2011 | Muhlsteff et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132363 A1 | 6/2011 | Chalvignac |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0197884 A1 | 8/2011 | Duff et al. |
| 2011/0197886 A1 | 8/2011 | Guttmann et al. |
| 2011/0197892 A1 | 8/2011 | Koledin |
| 2011/0203598 A1 | 8/2011 | Favet et al. |
| 2011/0209702 A1 | 9/2011 | Vuong et al. |
| 2011/0209704 A1 | 9/2011 | Jafari et al. |
| 2011/0209706 A1 | 9/2011 | Truschel et al. |
| 2011/0209707 A1 | 9/2011 | Terhark |
| 2011/0213215 A1 | 9/2011 | Doyle et al. |
| 2011/0226248 A1 | 9/2011 | Duff et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |

(56) References Cited

U.S. PATENT DOCUMENTS

| | | |
|---|---|---|
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0042869 A1 | 2/2013 | Andrieux et al. |
| 2013/0047983 A1 | 2/2013 | Andrieux et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0152923 A1 | 6/2013 | Andrieux et al. |
| 2013/0158370 A1 | 6/2013 | Doyle et al. |
| 2013/0159912 A1 | 6/2013 | Baker, Jr. |
| 2013/0167842 A1 | 7/2013 | Jafari et al. |
| 2013/0167843 A1 | 7/2013 | Kimm et al. |
| 2013/0186397 A1 | 7/2013 | Patel |
| 2013/0186400 A1 | 7/2013 | Jafari et al. |
| 2013/0186401 A1 | 7/2013 | Jafari et al. |
| 2013/0192599 A1 | 8/2013 | Nakai et al. |
| 2013/0220324 A1 | 8/2013 | Jafari et al. |
| 2013/0233314 A1 | 9/2013 | Jafari et al. |
| 2013/0233319 A1 | 9/2013 | Winter et al. |
| 2013/0239038 A1 | 9/2013 | Skidmore et al. |
| 2013/0239967 A1 | 9/2013 | Jafari et al. |
| 2013/0255682 A1 | 10/2013 | Jafari et al. |
| 2013/0255685 A1 | 10/2013 | Jafari et al. |
| 2013/0276788 A1 | 10/2013 | Masic |
| 2013/0283197 A1 | 10/2013 | Skidmore |
| 2013/0284172 A1 | 10/2013 | Doyle et al. |
| 2013/0284173 A1 | 10/2013 | Masic et al. |
| 2013/0284177 A1 | 10/2013 | Li et al. |
| 2013/0327331 A1 | 12/2013 | Bourdon |
| 2013/0333697 A1 | 12/2013 | Carter et al. |
| 2013/0333703 A1 | 12/2013 | Wallace et al. |
| 2013/0338514 A1 | 12/2013 | Karst et al. |
| 2013/0345532 A1 | 12/2013 | Doyle et al. |
| 2014/0000606 A1 | 1/2014 | Doyle et al. |
| 2014/0012150 A1 | 1/2014 | Milne et al. |
| 2014/0034054 A1 | 2/2014 | Angelico et al. |
| 2014/0034056 A1 | 2/2014 | Leone et al. |
| 2014/0041656 A1 | 2/2014 | Jourdain et al. |
| 2014/0048071 A1 | 2/2014 | Milne et al. |
| 2014/0048072 A1 | 2/2014 | Angelico et al. |
| 2014/0121553 A1 | 5/2014 | Milne et al. |
| 2014/0123979 A1 | 5/2014 | Doyle et al. |
| 2014/0130798 A1 | 5/2014 | Milne et al. |
| 2014/0182590 A1 | 7/2014 | Platt et al. |
| 2014/0224250 A1 | 8/2014 | Sanchez et al. |
| 2014/0251328 A1 | 9/2014 | Graboi et al. |
| 2014/0261409 A1 | 9/2014 | Dong et al. |
| 2014/0261410 A1 | 9/2014 | Sanchez et al. |
| 2014/0261424 A1 | 9/2014 | Doyle et al. |
| 2014/0276176 A1 | 9/2014 | Winter |
| 2014/0290657 A1 | 10/2014 | Vandine et al. |
| 2014/0309507 A1 | 10/2014 | Baker, Jr. |
| 2014/0345616 A1 | 11/2014 | Masic |
| 2014/0360497 A1 | 12/2014 | Jafari et al. |
| 2014/0366879 A1 | 12/2014 | Kimm et al. |
| 2014/0373845 A1 | 12/2014 | Dong |
| 2015/0034082 A1 | 2/2015 | Kimm et al. |
| 2015/0045687 A1 | 2/2015 | Nakai et al. |
| 2015/0090258 A1 | 4/2015 | Milne et al. |
| 2015/0090264 A1 | 4/2015 | Dong |
| 2015/0107584 A1 | 4/2015 | Jafari et al. |
| 2016/0045694 A1 | 2/2016 | Esmaeil-zadeh-azar |
| 2016/0114115 A1 | 4/2016 | Glenn et al. |

OTHER PUBLICATIONS

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

Hari, "Flow Sensor Fault Causing Ventilator Malfunction", Anaesthesia, 2005, 60, pp. 1042-2052; http://onlinelibrary.wiley.com/doi/10.1111/j.1365-2044.2005.04396.x/pdf; Accessed Jan. 16, 2015).

PCT International Preliminary Report on Patentability in International Application PCT/US2016/014131, dated Aug. 3, 2017, 7 pgs.

SYSTEMS AND METHODS FOR VENTILATION WITH UNKNOWN EXHALATION FLOW

INTRODUCTION

Medical ventilator systems are used to provide ventilatory and supplemental oxygen support to patients. Ventilators typically comprise a source of pressurized oxygen which is fluidly connected to the patient through a conduit or tubing. As each patient may require a different ventilation strategy, ventilators can be customized for the particular needs of an individual patient. For example, several different ventilator modes or settings have been created to provide better ventilation for patients in various different scenarios, such as mandatory ventilation modes and assist control ventilation modes.

VENTILATION WITH UNRELIABLE EXHALATION FLOW AND/OR EXHALATION PRESSURE

This disclosure describes systems and methods for providing novel ventilation that allows the patient to trigger or initiate the delivery of a breath. Further, this disclosure describes systems and methods for triggering ventilation when exhalation flow is unknown or unreliable by the ventilator.

In part, this disclosure describes a method for ventilating a patient with a ventilator. The method includes:
  delivering a fixed base flow;
  monitoring an exhalation flow, an exhalation pressure, and an exhalation auxiliary pressure during ventilation of the patient with the ventilator to determine a monitored exhalation flow, a monitored exhalation pressure, and a monitored exhalation auxiliary pressure;
  detecting a first trigger condition based at least on the monitored exhalation flow;
  triggering inspiration in response to the detecting of the first trigger condition;
  determining an absence of the monitored exhalation flow; and in response to the determining:
    ceasing to utilize the first trigger condition based at least on the exhalation flow;
    estimating the exhalation flow based on the monitored exhalation pressure and the monitored exhalation auxiliary pressure to determine an estimated exhalation flow;
    detecting a second trigger condition based at least on the estimated exhalation flow; and
    triggering inspiration during the ventilation in response to the detecting of the second trigger condition.

Yet another aspect of this disclosure describes a ventilator system that includes: a pressure generating system; a ventilation tubing system including a patient interface for connecting the pressure generating system to a patient; an exhalation valve connected to the ventilation tubing system; a plurality of sensors operatively coupled to at least one of the pressure generating system, the patient, and the ventilation tubing system; an exhalation flow estimation module, a driver; a main trigger module; a backup trigger module; and a controller. The pressure generating system generates a flow of breathing gas including a fixed base flow. The plurality of sensors monitors inspiratory pressure, inspiratory flow, exhalation pressure, exhalation auxiliary pressure, and/or exhalation flow to determine a monitored inspiratory pressure, a monitored inspiratory flow, a monitored exhalation pressure, a monitored exhalation auxiliary pressure, and a monitored exhalation flow. The exhalation flow estimation module estimates the exhalation flow based on the monitored exhalation pressure and the monitored exhalation auxiliary pressure to determine an estimated exhalation flow. The driver controls the exhalation valve to deliver ventilation to the patient based at least on at least one of the monitored exhalation flow and the estimated exhalation flow determined based on the exhalation pressure and the exhalation auxiliary pressure. The main trigger module triggers inspiration based on a first of at least one of the following events to occur: detection of a first trigger condition; and expiration of a predetermined amount of exhalation time. The backup trigger module triggers inspiration based on a first of at least one of the following events to occur: detection of a second trigger condition based at least on the estimated exhalation flow; and expiration of the predetermined amount of exhalation time. The controller determines an absence in the monitored exhalation flow and switches from the main trigger module to the backup trigger module.

Yet another aspect of this disclosure describes a method for ventilating a patient with a ventilator. The method includes:
  monitoring an exhalation flow, an exhalation pressure, and an exhalation auxiliary pressure during ventilation of the patient with the ventilator to determine a monitored exhalation flow, a monitored exhalation pressure, and a monitored exhalation auxiliary pressure;
  delivering ventilation based at least on the monitored exhalation flow;
  determining an absence in the monitored exhalation flow;
  in response to the absence of the monitored exhalation flow, estimating the exhalation flow based at least on the monitored exhalation pressure to determine an estimated exhalation flow; and
  in response to the absence of the monitored exhalation flow, ceasing to deliver the ventilation based at least on the monitored exhalation flow and instead delivering ventilation based at least on the estimated exhalation flow.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments of systems and methods described below and are not meant to limit the scope of the invention in any manner, which scope shall be based on the claims.

DETAILED DESCRIPTION

Figure 1A:
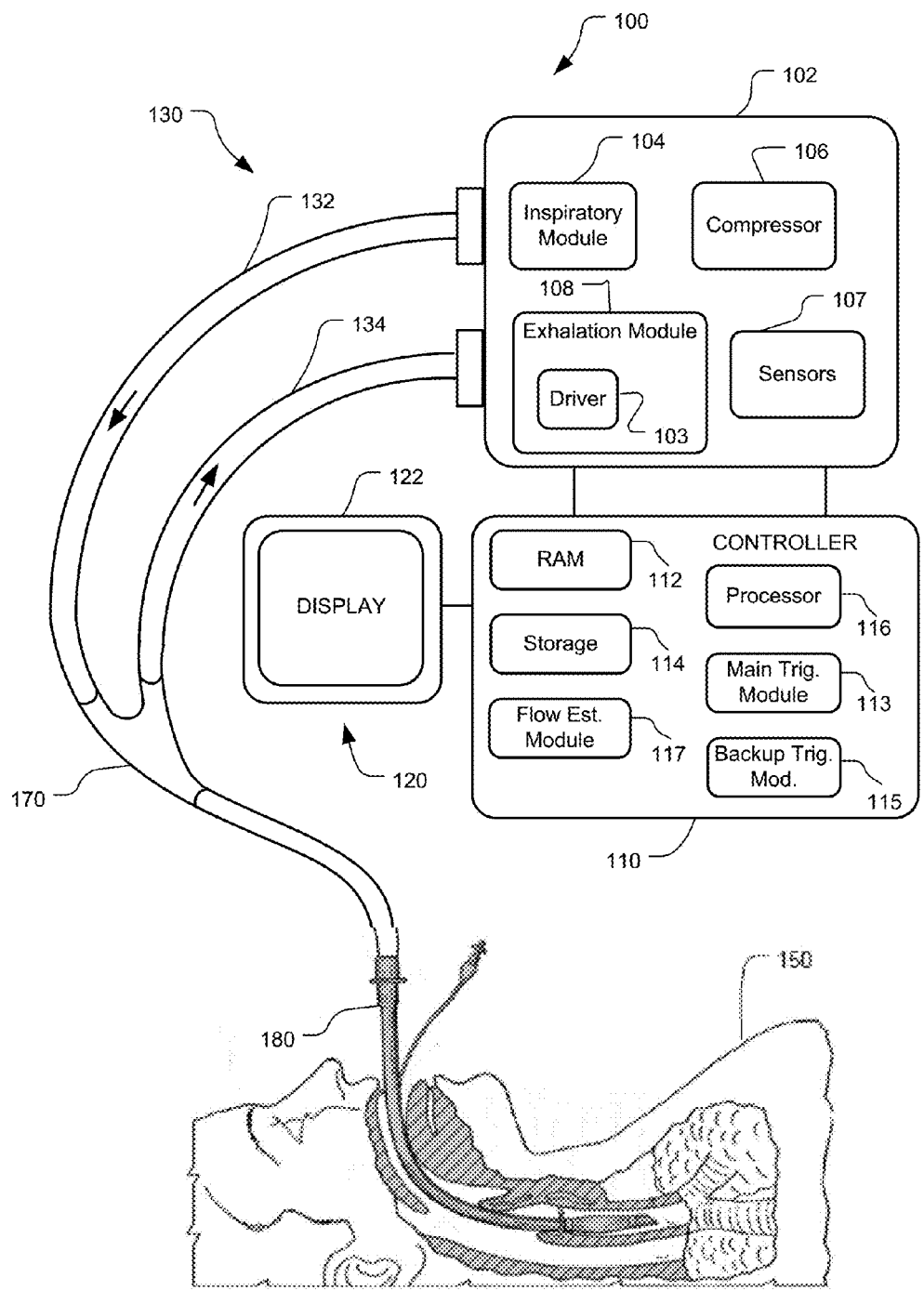
FIG. 1A is a diagram illustrating an embodiment of an exemplary ventilator.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

As each patient may require a different ventilation strategy, ventilators can be customized for the particular needs of an individual patient. For example, several different ventilator modes or settings have been created to provide better ventilation for patients in various different scenarios, such as mandatory ventilation modes and assist control ventilation modes. Assist control modes allow a spontaneously breathing patient to trigger inspiration during ventilation.

The response performance of a medical ventilator to a patient trigger from exhalation into inhalation phase represents an important characteristic of a medical ventilator. A ventilator's trigger response impacts the patient's work of breathing and the overall patient-ventilator synchrony. The trigger response performance of a ventilator is a function of a patient's inspiratory behavior (breathing effort magnitude and timing characteristics) as well as the ventilator's gas delivery dynamics, flow control parameters (actuator response, dead bands, etc.), and triggering algorithm.

In conventional flow triggering modes, a patient's inspiratory trigger is detected based on the magnitude of flow deviations generated by the patient's inspiratory effort. In a flow triggering mode, the ventilator delivers a fixed base flow during the exhalation phase. Accordingly, flow deviations are sensed by the computation of the ventilator net flow (base flow-exhausted flow) and compared against a set trigger threshold for triggering. As used herein, a trigger condition is met when a situation occurs that should trigger the delivery of a breath. For example, a trigger condition is met when a trigger threshold is breached, or exceeded, a predetermined amount of time has expired, and/or exhalation flow becomes stable.

Base flow is the delivered flow during exhalation and consists of a desired combination of appropriate gases. A fixed base flow may be generated by a controller regulating an actuator (valve) to maintain a constant desired flow rate from a regulated pressurized gas source into the ventilator circuit. The magnitude or the flow rate generated by the regulator at different open positions is determined by an inspiratory flow sensor. Therefore, base flow is determined by the ventilator by measuring the amount of flow delivered to the patient via an inspiration flow sensor during exhalation.

Exhausted flow is measured during the expiratory phase of a ventilator breath while a base flow is delivered through the patient circuit. The terms "expiratory" and "exhalation" are utilized interchangeably herein. Accordingly, the term "expiratory" encompasses the term "exhalation" and the term "exhalation" encompasses "expiratory." The terms "expiratory" and "exhalation" are used herein denote the phase of a patient breath immediately following the inspiration phase during which the patient exhales gas from his or her lungs. To determine the volume of gas exhaled by the patient, the net flow (total delivered flow minus total flow through exhalation module) is used for integration. That is, the delivered base flow is subtracted from the sum of the base flow and patient flow exiting through the exhalation port. The flow exiting the exhalation module during the active phase of patient exhalation is the sum of base flow delivered by the ventilator and exhaled flow from the patient lung.

In the event of malfunctions and/or system failures in ventilators, ventilators, typically, sound an alarm and stop ventilation. Ventilators stop ventilation because the necessary parameters for delivering the desired ventilation are unreliable or undeterminable due to the malfunction.

For example, the ventilator utilizes several systems and/or components to control the spontaneous triggering of the delivery of a breath to the patient, such as the source of gas, the inspiratory conduit and valve, the inspiratory module, exhalation conduit and valve, an exhalation module, and a controller. The expiratory module utilizes measured expiratory flow and/or expiratory pressure to control the exhalation valve to deliver the desired amount of flow and/or pressure during inspiration and exhalation. For example, the controller controls when to deliver inspiration based on spontaneous effort from the patient which can be determined by exhalation flow. If exhalation flow is unavailable, the ventilator is unable to determine when to trigger delivery of a breath to the patient and therefore ceases ventilation. However, it is desirable to provide ventilation to a patient whose ability to breathe on his or her own is impaired. Accordingly, the systems and methods disclosed herein provide ventilation and maintain comfortable patient-ventilator synchrony in the event that an exhalation flow is unavailable.

In some embodiments, the exhalation module includes a removable exhalation flow sensor. The exhalation flow sensor may be removed to be cleaned and/or replaced. In the absence of an exhalation flow sensor, under fault conditions, or during a malfunction of the exhalation flow sensor, the exhalation flow is unknown or unreliable. Therefore, monitored exhalation flow is unreliable or undeterminable, so a conventional flow triggering algorithm cannot be used to compare the net flow (base flow–exhausted flow) against the trigger threshold. Accordingly, patient initiated triggers cannot be detected by ventilators utilizing conventional triggering methods and prevented the use of a spontaneous mode of ventilation in these ventilators while the exhalation flow sensor was removed or malfunctioning. However, the systems and methods as described herein utilize monitored expiratory pressure and/or monitored expiratory auxiliary pressure to estimate an exhalation flow, when exhalation flow is undeterminable.

An example of a fault condition is presented by the Exhalation Back-Up Ventilation (EBUV) mode under which the data measurement and acquisition subsystem calculate an estimated exhalation flow because the data from the exhalation flow sensor is unavailable and/or unreliable. As discussed above, most conventional ventilators declare an alarm and terminate ventilation. However, the EBUV mode allows a ventilator to continue ventilating the patient under such conditions, thereby maintaining a reduced work of breathing and increased patient-ventilator synchrony when compared to conventional ventilators.

Accordingly, the systems and methods described herein provide for a triggering mechanism when an exhalation flow is undeterminable/unavailable by the ventilator. For example, the exhalation flow is undeterminable by the ventilator when a malfunction is detected in the exhalation flow sensor, and/or when the exhalation flow sensor is removed for cleaning and/or replacement. The capability of triggering without the exhalation flow allows an EBUV mode to maintain comfortable patient-ventilator synchrony. The systems and methods described herein provide a triggering mechanism for a spontaneous patient when the ventilator cannot determine the exhalation flow. The ventilator estimates an exhalation flow based on monitoring exhalation pressure and/or exhalation auxiliary pressure. The estimated exhalation flow is substituted for the actual exhalation flow allowing the traditional flow triggering algorithm to be utilized. For example, the ventilator is able to determine flow deviations by the computation of the ventilator net flow (base flow-estimated exhausted flow) which is compared against a set trigger threshold for triggering.

Figure 1B:
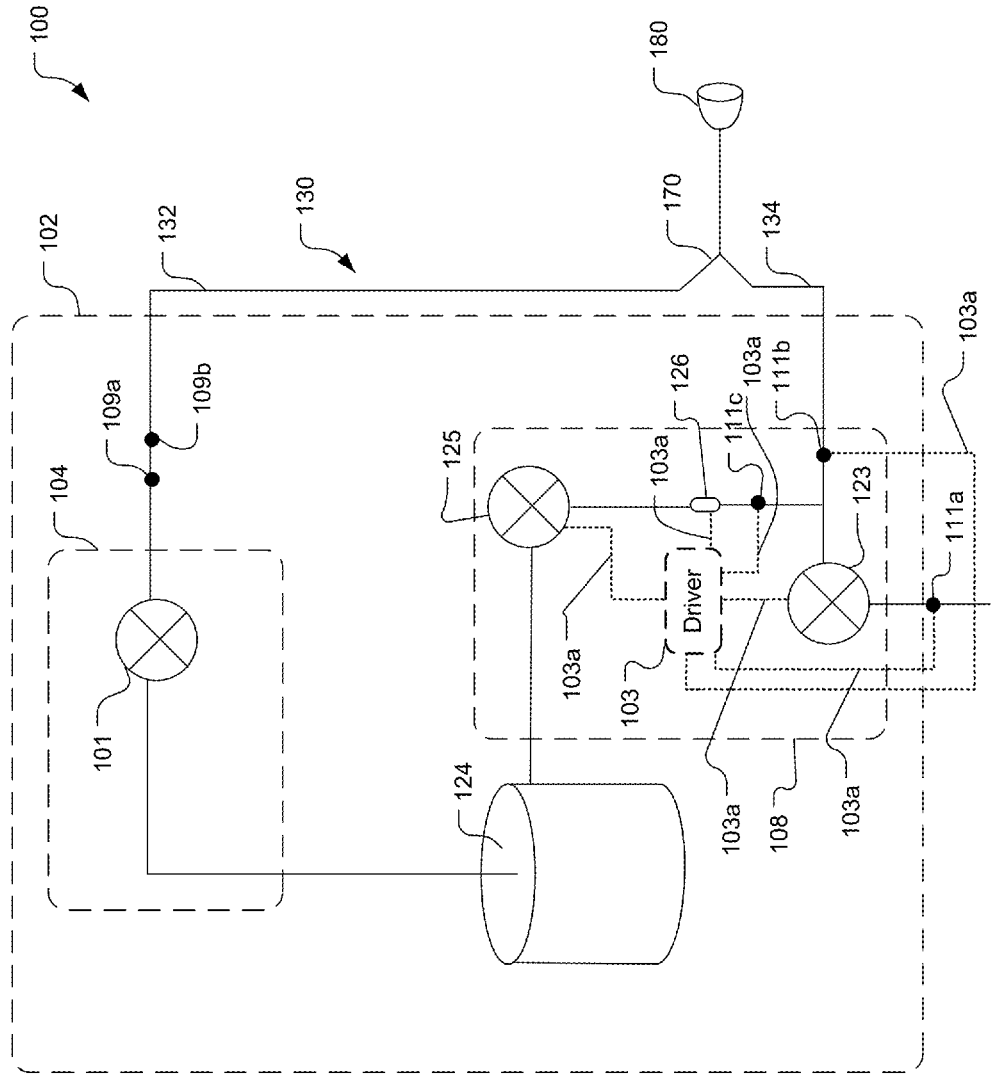
FIG. 1B illustrates an embodiment of the ventilator shown in FIG. 1A.

FIGS. 1A and 1B are diagrams illustrating an embodiment of an exemplary ventilator 100. The exemplary ventilator 100 illustrated in FIG. 1A is connected to a human patient 150. The ventilator 100 includes a pneumatic system 102 (also referred to as a pressure generating system 102) for circulating breathing gases to and from the patient 150 via a ventilation tubing system 130, which couples the patient 150 to the pneumatic system 102 via an invasive (e.g., endotracheal tube, as shown) or a non-invasive (e.g., nasal mask) patient interface 180. The pneumatic system 102 delivers ventilation to the patient 150 according to predetermined or selected modes (spontaneous, assist, mandatory, etc.) and breath types (pressure control, pressure support, pressure assist, volume control, volume support, volume-controlled-pressure-targeted, etc.).

The ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple the patient interface 180 (shown as an endotracheal tube in FIG. 1A and as a nasal mask in FIG. 1B) to an inspiratory limb 132 and an exhalation limb 134 of the ventilation tubing system 130.

The pneumatic system 102 may be configured in a variety of ways. In the present example, the pneumatic system 102 includes an exhalation module 108 coupled with the exhalation limb 134 and an inspiratory module 104 coupled with the inspiratory limb 132. A compressor 106, accumulator 124 (as illustrated in FIG. 1B) and/or other source(s) of pressurized gases (e.g., air, oxygen, and/or helium) is coupled with the inspiratory module 104 and the exhalation module 108 to provide a gas source for ventilatory support via the inspiratory limb 132. In an embodiment, the pneumatic system 102 is operatively coupled with, and at times receives directions from, a controller 110.

The inspiratory module 104 is configured to deliver gases to the patient 150 and/or through the inspiratory limb 132 according to prescribed ventilatory settings. The inspiratory module 104 is associated with and/or controls an inspiratory delivery valve 101 for controlling gas delivery to the patient 150 and/or gas delivery through the inspiratory limb 132 as illustrated in FIG. 1B. In some embodiments, the inspiratory module 104 is configured to provide ventilation according to various ventilator modes, such as mandatory and assist modes.

The exhalation module 108 is configured to release gases from the patient's lungs and/or exhalation circuit according to prescribed ventilatory settings. Accordingly, the exhalation module 108 also controls gas delivery through the inspiratory limb 132 and the exhalation limb 134. The exhalation module 108 controls an exhalation valve 123 to maintain the prescribed patient's airway pressure and release the flow from the patient's lungs.

The ventilator 100 may include a driver 103 for controlling the exhalation valve 123, the exhalation drive valve 125, and/or an exhalation pump 126, such as jet pump. In some embodiments, the driver 103 is part of the exhalation module 108 as illustrated in FIGS. 1A and 1B. In other embodiments, the driver 103 is included in a different system or module of the ventilator 100, such as the pneumatic system 102 or controller 110. The driver 103 controls the exhalation valve 123 to relieve the over pressure delivered during inhalation to achieve the desired inspiration pressure. Further, the driver 103 controls the exhalation valve 123 to deliver the desired PEEP during exhalation. In some embodiments, the driver 103 is controlled based on a control algorithm that is computed by utilizing monitored exhalation pressure and monitored exhalation flow. The monitored exhalation flow and pressure are determined by one or more of a plurality of sensors 107, which are discussed in further detail below.

In some embodiments, the driver 103 is a differential driver. In other embodiments, the driver 103 is a pulse width modulation driver. The above listed drivers are not meant to be limiting. Any suitable driver for controlling an exhalation module 108 in a ventilator may be utilized by the ventilator 100.

In some embodiments, as illustrated in FIG. 1B, the driver circuit 103a of the driver 103 is communicatively coupled to the exhalation valve 123 and one or more expiratory sensors, such as an expiratory flow sensor 111a, an expiratory pressure sensor 111b, and an exhalation auxiliary pressure sensor 111c as illustrated in FIG. 1B. In further embodiments, the driver circuit 103a of the driver 103 is communicatively coupled to an exhalation pump 126 and exhalation drive valve 125, such as a solenoid valve, that are located upstream of the exhalation auxiliary pressure sensor 111c. Further, the driver 103 is communicatively coupled to other systems and modules of the ventilator 100 such as the exhalation module 108, inspiratory module 104, and/or controller 110.

The expiratory pressure sensor 111b and the exhalation auxiliary pressure sensor 111c are pressure sensors that monitor gas pressure at different locations in the exhalation limb 134. The exhalation pressure sensor 111b is located directly in the exhalation flow path from the patient and monitors gas pressure from the patient to determine a monitored exhalation pressure. The exhalation auxiliary pressure sensor 111c is any pressure sensor in addition to the exhalation pressure sensor 111b located at a second location that is different than the location of the exhalation pressure sensor 111b within the exhalation limb 134. In some embodiments, the exhalation auxiliary pressure sensor 111c is an exhalation drive pressure sensor as illustrated in FIG. 1B. The exhalation drive pressure sensor is a sensor that is located away from the exhalation flow path (or not directly in-line with the exhalation flow path) from the patient and instead monitors gas pressure coming from the exhalation pump 126 and/or the exhalation drive valve 125 to determine a monitored exhalation drive pressure. Accordingly, the exhalation pressure or the monitored exhalation pressure is determined from readings from the exhalation flow sensor 111b. Further, the exhalation auxiliary pressure or the monitored exhalation auxiliary pressure is determined from readings from the exhalation auxiliary pressure sensor 111c. Additionally, the exhalation drive pressure or the monitored exhalation drive pressure (a type of exhalation auxiliary pressure) is determined from readings from an exhalation drive pressure sensor (a type of auxiliary pressure sensor 111c).

The ventilator 100 also includes a main trigger module 113 that triggers inspiration according to prescribed ventilatory settings. In some embodiments, as illustrated in FIG. 1A, the main trigger module 113 is included in a controller 110. In other embodiments the main trigger module 113 is included in a different system or module, such as the pneumatic system 102. In an embodiment, the main trigger module 113 triggers an inspiration based on the first of at least two events, such as the expiration of a predetermined amount of time and detection of a first trigger condition. In other embodiments, the main trigger module 113 triggers an inspiration based on the expiration of a predetermined amount of exhalation time and/or the detection of a first trigger condition.

There are several different trigger types or systems and/or methods utilized by the ventilator 100 for detecting a first trigger condition. In some embodiments, a trigger type for detecting patient effort may be selected or input by an operator. In some embodiments, the trigger type is automatically selected by the ventilator. Any suitable type of triggering detection for determining a patient trigger may be utilized by the ventilator, such as nasal detection, diaphragm detection, and/or brain signal detection. Further, the ventilator may detect patient triggering via a pressure-monitoring method, a flow-monitoring method, direct or indirect measurement of neuromuscular signals, or any other suitable method. Sensors 107 suitable for this detection may include any suitable sensing device as known by a person of skill in the art for a ventilator. In addition, the sensitivity of the ventilator to changes in pressure and/or flow may be adjusted such that the ventilator may properly detect the patient effort, i.e., the lower the pressure or flow change setting the more sensitive the ventilator may be to patient triggering.

Alternatively, the ventilator may detect a flow-triggered event. Specifically, the ventilator may monitor the circuit flow, as described above. If the ventilator detects a slight drop in flow during exhalation, this may indicate, again, that the patient is attempting to inspire. In this case, the ventilator is detecting a drop in baseline flow (or base flow) attributable to a slight redirection of gases into the patient's lungs (in response to a slightly negative pressure gradient as discussed above). Base flow refers to a constant flow existing in the circuit during exhalation that enables the ventilator to detect expiratory flow changes and patient triggering. For example, while gases are generally flowing out of the patient's lungs during exhalation, a drop in flow may occur as some gas is redirected and flows into the lungs in response to the slightly negative pressure gradient between the patient's lungs and the body's surface. Thus, when the ventilator detects a slight drop in flow below the base flow by a predetermined threshold amount (e.g., 2 L/min below base flow), it may interpret the drop as a patient trigger and may consequently initiate inspiration by delivering respiratory gases.

In one embodiment, the ventilator 100 is preconfigured to deliver an inspiration after a predetermined amount of exhalation time to prevent the patient 150 from becoming under-ventilated. Accordingly, the predetermined amount of exhalation time (e.g., known as an apnea interval in some ventilators) is the trigger threshold in this embodiment. For example, the main trigger module 113 will automatically trigger an inspiration after 20 seconds, 30 seconds, or 60 seconds of exhalation time. In some embodiments, the predetermined amount of time is determined by the clinician and/or ventilator 100 based on whether the patient 150 is an infant, child, adult, male, female, and/or suffering from a specific disease state.

The ventilator 100 includes a flow estimation module 117 that estimates an exhalation flow when a malfunction detected by the controller 110 establishes that the exhalation flow is undeterminable or unreliable. In some embodiments, as illustrated in FIG. 1A, the controller 110 includes the flow estimation module 117. In other embodiments, the pneumatic system 102 includes the flow estimation module 117. The terms "undeterminable" and "unreliable", while having different meanings, are utilized interchangeably herein. Accordingly, the term "unreliable" encompasses the term "undeterminable" and the term "undeterminable" encompasses "unreliable." In previous systems, if the exhalation flow was not determinable or if the exhalation flow sensor 111a was removed, ventilators utilizing conventional triggering methods could no longer deliver spontaneous ventilation. In order to provide spontaneous ventilation, the ventilator 100 estimates exhalation flow based on the monitored exhalation pressure and/or the monitored exhalation auxiliary pressure as determined by one or more of the plurality of sensors 107. Since an exhalation flow is estimated, the ventilator 100 may continue to spontaneously ventilate, maintaining patient-ventilator synchrony and/or patient comfort. In some embodiments, the flow estimation module 117 is a part of the exhalation module 108 and is communicatively coupled to the exhalation flow sensor 111a, an exhalation pressure sensor 111b and/or an exhalation auxiliary pressure sensor 111c. In other embodiments, the flow estimation module 117 is a part of the inspiratory module 104 or the controller 110. The flow estimation module 117 may also be communicatively coupled to a backup trigger module 115.

In some embodiments, the flow estimation module 117 determines the estimated exhalation flow utilizing the following Equation #1:

$$P_{exp} - P_{drv} = a \cdot Q_{exp}^2 + b \cdot Q_{exp} + c, \quad (\#1)$$

where, $P_{exp}$=measured expiratory pressure value in cmH2O;
$P_{drv}$=measured exhalation auxiliary pressure value in cmH2O;
$Q_{exp}$=measured exhalation flow (EVQ) value in 1 pm; and
a, b, c=constant coefficients.

In order to utilize Equation #1, the constant flow coefficients are determined by the ventilator 100 or the flow estimation module 117 during a calibration test while the exhalation flow is determinable. The calibration test includes measuring and storing the values of $P_{exp}$ and $P_{drv}$ while delivering constant exhalation flow. This test may repeats three times by delivering different exhalation flow each time. The stored $P_{exp}$, $P_{drv}$, and $Q_{exp}$ are used to obtain the constant coefficients a, b, and c by solving Equation #1 listed above. Once the constant coefficients are determined for a patient, the determined constant coefficients are stored by the ventilator 100 or the flow estimation module 117 until needed. When the controller 110 detects that the monitored exhalation flow and is undeterminable or unreliable, the flow estimation module 117 derives Equation #2, listed below, from Equation #1 to determine the estimated exhalation flow:

$$\widehat{Q_{exp}} = \frac{-b \pm \sqrt{b^2 - 4b(c - P_{exp} + P_{drv})}}{2a}, \quad (\#2)$$

where, $\widehat{Q_{exp}}$ =estimated exhalation flow (EVQ) value in 1 pm.

Because the exhalation flow is not determinable during a removal or malfunction of the exhalation flow sensor 111a, the amount of PEEP delivered may be determined based on the estimated exhalation flow. Further, the estimated exhalation flow is used in an inspiration control algorithm by the inspiration module 104 to deliver the desired inspiration pressure. The driver 103 is controlled based on an exhalation control algorithm to deliver the PEEP that is computed by utilizing the estimated exhalation flow. The monitored exhalation pressure and/or auxiliary pressure are determined by one or more of the plurality of sensors 107. In some embodiments, the monitored exhalation pressure and/or exhalation auxiliary pressure are determined by the exhalation pressure sensor 111b and the exhalation auxiliary pressure sensor 111c.

In further embodiments, other parameters usually determined or calculated by utilizing the exhalation flow are determined by utilizing the estimated exhalation flow, when the exhalation flow is undeterminable. For example, an estimated exhaled tidal volume may be determined utilizing the estimated exhalation flow. In some embodiments, the flow estimation module 117 determines these additional estimated parameters based on the estimated exhalation flow. In other embodiments, the controller 110 or pneumatic system 102 determines these additional estimated parameters based on the estimated exhalation flow. These estimated parameters, such as an estimated exhalation tidal volume, are communicated to other components of the ventilator 100, such as the display 122.

Further, in some embodiments, the ventilator 100 includes a backup trigger module 115. In some embodiments, the backup trigger module 115 triggers inspiration according to prescribed ventilatory settings while the ventilator is in the EBUV mode. The controller 110 utilizes the backup trigger module 115 when a malfunction or a removal of the exhalation flow sensor 111a is detected by the ventilator 100 or a subsystem of the ventilator, such as the controller 110. The malfunction/removal prevents the monitored exhalation flow from being determined. In some embodiments, as illustrated in FIG. 1A, the controller 110 includes the backup trigger module 115. In other embodiments, the pneumatic system 102 includes the backup trigger module 115.

In some embodiments, the backup trigger module 115 triggers inspiration based on the first of at least two events, such as the expiration of a predetermined amount of time and the detection of a second trigger condition. In other embodiments, the backup trigger module 115 triggers inspiration based on the expiration of a predetermined amount of time and/or the detection of a second trigger condition. In some embodiments, the second trigger condition is a trigger threshold based on a flow deviation. In another embodiment, the second trigger condition is an inspiratory trigger threshold. In an embodiment, the backup trigger module 115 utilizes a fixed base flow, such as but not limited to 1.5 LPM, delivered by the pneumatic system 102 and an estimated exhalation flow, estimated by the flow estimation module 117, to determine a flow deviation, or net flow, which is compared to the trigger threshold. If the flow deviation breaches the trigger threshold then the controller 110 instructs the pneumatic system 102 to deliver a breath.

In some embodiments, the flow deviation is determined by adding or subtracting one of the fixed base flow and the estimated exhalation flow from the other. Because the exhalation flow is not determinable, an estimated exhalation flow is used to determine a flow deviation to be compared to the trigger threshold. The use of estimated exhalation flow allows the ventilator to continue triggering spontaneous breaths for the patient therefore maintaining patient-ventilator synchrony and patient comfort. The estimated exhalation flow is determined by the flow estimation module 117. In an embodiment, if the backup trigger module 115 determines that ventilator and/or patient parameters meet and/or exceed an inspiration trigger threshold during exhalation, the backup trigger module 115 instructs the inspiratory module 104 to deliver an inspiration, which effectively ends the exhalation phase. In another embodiment the backup trigger module 115 is included in a different system such as the pneumatic system 102.

If the backup trigger module 115 determines that ventilator and/or patient parameters do not meet and/or exceed an inspiration trigger threshold during exhalation, the backup trigger module 115 continues to monitor the ventilator and/or patient parameters and compare them to a trigger threshold until the ventilator and/or patient parameters meet and/or exceed a trigger threshold, an exhalation flow is determinable, or until the expiration of a predetermined amount of exhalation time. If a trigger threshold is not breached within a predetermined amount of time, then the ventilator 100 will deliver a breath at the expiration of the predetermined amount of exhalation time. In some embodiments, the predetermined amount of exhalation time, such as but not limited to 20 seconds, 30 seconds, or 60 seconds of exhalation time, starts to elapse upon the delivery of a breath. The predetermined amount of time may be input by the clinician or calculated by the ventilator.

In another embodiment, the second trigger condition is met when the patient 150 reaches a stable portion of exhalation as determined by the backup trigger module 115. In order to determine a stable portion of exhalation, the ventilator 100 monitors the estimated exhalation flow. In some embodiments, the backup trigger module 115 collects multiple exhalation flow estimates for a set period during exhalation after the expiration of a restricted period. The restricted period as used herein is a predetermined time period that starts at the beginning of exhalation. The patient 150 is prevented from triggering ventilation during the predetermined time period of the restricted period. For example, the restricted period may be 25 ms, 50 ms, 100 ms, 200 ms, and/or any other suitable time period for preventing the patient 150 from triggering inspiration. In other embodiments, the backup trigger module 115 determines a stable portion of exhalation without utilizing a restricted period. In an embodiment, the backup trigger module 115 determines stability by monitoring the estimated exhalation flow every computation cycle. In some embodiments, the computational cycle is every 5 ms. If the difference between two successive exhalation flow estimates is zero, or about zero, then a stable portion of exhalation has been determined and the backup trigger module 115 will instruct the ventilator 100 to deliver a breath. In an additional embodiment, the second trigger condition is met when the patient 150 after reaching a stable portion of exhalation detects a negative change in base flow as determined by the backup trigger module 115.

In some embodiments, the trigger modules 113, 115 utilize a change in flow rate as an inspiration trigger threshold. For example, the inspiration trigger threshold may be a change in flow rate of −1.5 liters per minute (LPM), −2 LPM, −3 LPM, −4 LPM, −5 LPM, −6 LPM, −7 LPM, and −8 LPM or may be a range of a change in flow rate, such as a range of −3 LPM to −6 LPM or −4 LPM to −7 LPM. This list is exemplary only and is not meant to be limiting. Any suitable changes in flow rate may be utilized by the trigger modules 113, 115 for triggering an inspiration. For example, in some embodiments, the trigger threshold is any detected drop in flow rate that is at least 1.5 LPM.

The controller 110 is operatively coupled with the pneumatic system 102, signal measurement and acquisition systems such as but not limited to a plurality of sensors 107, and an operator interface 120 that may enable an operator to interact with the ventilator 100 (e.g., change ventilator settings, select operational modes, view monitored parameters, etc.).

In some embodiments, the controller 110 includes memory 112, one or more processors 116, storage 114, and/or other components of the type commonly found in command and control computing devices, as illustrated in FIG. 1A. In alternative embodiments, the controller 110 is a separate component from the operator interface 120 and pneumatic system 102. In other embodiments, the controller 110 is located in other components of the ventilator 100, such as in the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Further, the controller 110 determines if the exhalation flow undeterminable and/or unreliable. Accordingly, the controller 110 determines if the exhalation flow sensor 111a has been removed or if the exhalation flow sensor 111a is malfunctioning. If the exhalation flow sensor 111a is determined to be removed and/or malfunctioning by the controller 110, then the monitored expiratory flow is unreliable.

Several different systems and methods are currently utilized and known in the art for determining a malfunction in a sensor or for determining if a sensor has been removed. The controller 110 detects a malfunction or a removal utilizing any of these known systems or methods. For example, malfunctions or removals may be detected based on changes in voltages, temperatures, wattages, coefficients, humidity, and/or overcurrent for the exhalation flow sensor 111a of the exhalation module 108.

If the controller 110 determines that the exhalation flow is undeterminable, the controller 110 switches from, or instructs a switch from, the main trigger module 113 to the backup trigger module 115. In an embodiment, the backup trigger module 115 activates the flow estimation module 117 which estimates the exhalation flow based on the monitored inspiratory pressure and/or monitored inspiratory flow. The ventilator 100 is able to maintain a spontaneous breath mode of ventilation even when the exhalation flow sensor is removed or malfunctioning. During the spontaneous breath mode of ventilation, the inspiratory triggering is based on an estimated exhalation flow instead of a monitored exhalation flow. Further, the controller 110 instructs the pneumatic system 102 to deliver an EBUV mode of ventilation. The EBUV mode is a spontaneous mode of ventilation. The pressure to be administered to the patient 150 during inspiration and exhalation of the spontaneous breath is determined by the ventilator 100. Further, the inspiratory time, and respiratory rate for the patient 150 are also determined by the ventilator 100. These variables determine the pressure of the gas delivered to the patient 150 during each spontaneous breath inspiration and exhalation. For the EBUV mode, when the inspiratory time is equal to the prescribed inspiratory time, the ventilator 100 initiates exhalation. Exhalation lasts from the end of inspiration until an inspiratory trigger is detected or until the expiration of a predetermined amount of time. Upon the detection of an inspiratory trigger, another spontaneous breath is given to the patient 150.

During an EBUV mode, the ventilator 100 maintains the same pressure waveform at the mouth, regardless of variations in lung or airway characteristics, e.g., respiratory compliance and/or respiratory resistance. However, the volume and flow waveforms may fluctuate based on lung and airway characteristics. In some embodiments, the ventilator 100 determines the set pressure (including the inspiratory pressure and the PEEP), the inspiratory time, and respiration rate based on known ventilator parameters that have not been corrupted by the determined malfunction, such as weight, height, sex, age, and disease state. In other embodiments, the set pressure (including the inspiratory pressure and the PEEP), the inspiratory time, and the respiration rate are predetermined by the ventilator 100 upon the detection of an undeterminable exhalation flow and are the same for any patient 150 being ventilated by the ventilator 100.

If the controller 110 does not determine a malfunction or absence in the exhalation flow, the controller 110 does not change to the backup trigger module 115 and continues to trigger an inspiration utilizing the main trigger module 113. In some embodiments, if the controller 110 determines a malfunction or absence of the exhalation flow, the controller 110 switches to the backup trigger module 115 to trigger inspiration from the main trigger module 113. In some embodiments, the controller 110 is part of the exhalation module 108. In some embodiments, the controller 110 is part of the pneumatic system 102. In other embodiments, the controller 110 is a module separate from the pneumatic system 102.

The ventilator 100 also includes a plurality of sensors 107 communicatively coupled to the ventilator 100. The sensors 107 may be located in the pneumatic system 102, ventilation tubing system 130, and/or on the patient 150. The embodiment of FIG. 1A illustrates a plurality of sensors 107 in pneumatic system 102.

The sensors 107 may communicate with various components of the ventilator 100, e.g., the pneumatic system 102, other sensors 107, the exhalation module 108, the inspiratory module 104, a processor 116, the controller 110, and any other suitable components and/or modules. In one embodiment, the sensors 107 generate output and send this output to the pneumatic system 102, other sensors 107, the exhalation module 108, the inspiratory module 104, the processor 116, the controller 110, the main trigger module 113, the backup trigger module 115, the flow estimation module 117, and any other suitable components and/or modules.

The sensors 107 may employ any suitable sensory or derivative technique for monitoring one or more patient parameters or ventilator parameters associated with the ventilation of a patient 150. The sensors 107 may detect changes in patient parameters indicative of patient inspiratory or exhalation triggering effort, for example. The sensors 107 may be placed in any suitable location, e.g., within the ventilatory circuitry or other devices communicatively coupled to the ventilator 100. Further, the sensors 107 may be placed in any suitable internal location, such as, within the ventilatory circuitry or within components or modules of the ventilator 100. For example, the sensors 107 may be coupled to the inspiratory and/or exhalation modules 104, 108 for detecting changes in, for example, inspiratory flow, inspiratory pressure, expiratory pressure, and expiratory flow. In other examples, the sensors 107 may be affixed to the ventilatory tubing 130 or may be embedded in the tubing itself. According to some embodiments, the sensors 107 may be provided at or near the lungs (or diaphragm) for detecting a pressure in the lungs. Additionally or alternatively, the sensors 107 may be affixed or embedded in or near the wye-fitting 170 and/or patient interface 180. Any sensory device useful for monitoring changes in measurable parameters during ventilatory treatment may be employed in accordance with embodiments described herein.

For example, in some embodiments, the one or more sensors 107 of the ventilator 100 include an inspiratory flow sensor 109a and an exhalation flow sensor 111a as illustrated in FIG. 1B. In one embodiment, the inspiratory flow sensor 109a is located in the inspiratory limb 132 and is controlled by the inspiratory module 104 and/or the flow estimation module 117. However, the inspiratory flow sensor 109a may be located in any suitable position for monitoring inspiratory flow and may be monitored by any suitable ventilator component, such as the pressure generating system 102. In one embodiment, the exhalation flow sensor 111a is located in the exhalation limb 134 and is monitored by the exhalation module 108 and/or the controller 110, including the main trigger module 113 and/or the backup trigger module 115. However, the exhalation flow sensor 111a may be located in any suitable position for monitoring exhalation flow and may be monitored by any suitable ventilator component, such as the pressure generating system 102 and the driver 103. In some embodiments, the exhalation flow sensor 111a is removable and located downstream of the exhalation valve 123 as illustrated in FIG. 1B.

Further, in some embodiments, the one or more sensors 107 of the ventilator 100 also include an inspiratory pressure sensor 109b, an exhalation pressure sensor 111b, and/or an exhalation auxiliary pressure sensor 111c as illustrated in FIG. 1B. In one embodiment, the inspiratory pressure sensor 109b is located in the inspiratory limb 132 and is controlled by the inspiratory module 104 and the flow estimation module 117. However, the inspiratory pressure sensor 109b may be located in any suitable position for monitoring inspiratory pressure and may be monitored by any suitable ventilator component, such as the pressure generating system 102. In one embodiment, the exhalation pressure sensor 111b is located in the exhalation limb 134 and is monitored by the exhalation module 108 and/or the controller 110. However, the exhalation pressure sensor 111b may be located in any suitable position for monitoring exhalation pressure and may be monitored by any suitable ventilator component, such as the pressure generating system 102 and driver 103. In some embodiments, as illustrated in FIG. 1B, the exhalation pressure sensor 111b is located upstream of the exhalation pump 126 and/or the exhalation valve 123. The exhalation auxiliary pressure sensor 111c is located in the exhalation limb 134 downstream from the exhalation pump 126 and is monitored by the exhalation module 108 and/or the controller 110. However, the exhalation auxiliary pressure sensor 111c may be located in any suitable position for monitoring exhalation auxiliary pressure and may be monitored by any suitable ventilator component, such as the pressure generating system 102 and driver 103.

The exhalation pressure sensor 111b and the exhalation auxiliary pressure sensor 111c measure exhalation pressure, while the exhalation flow sensor 111a measures exhalation flow. The exhalation flow sensor 111a is a different type of sensor than the exhalation pressure sensor 111b and the exhalation auxiliary pressure sensor 111c.

As should be appreciated, with reference to the Equation of Motion, ventilatory parameters are highly interrelated and, according to embodiments, may be either directly or indirectly monitored. That is, parameters may be directly monitored by one or more sensors 107, as described above, or may be indirectly monitored or estimated by derivation according to the Equation of Motion or other known relationships In some embodiments, the sensor measurements are adjusted for error. In some embodiments, the exhalation flow sensor 111a is adjusted error. For example, during a flow calibration test, the exhalation flow sensor 111a readings may be compared to another more accurate flow sensor in the patient circuit 130. The difference between the exhalation flow sensor 111a measurement and this other flow sensor's measurement may be calculated and stored by the ventilator 100. In some embodiments, the inspiration flow sensor is more accurate than the exhalation flow sensor 111a and is utilized during the flow calibration test to calculate the exhalation flow sensor error. This stored difference should represent exhalation flow sensor 111a error and, as such, may be added to each exhalation flow sensor 111a measurement during ventilation of a patient after the calibration to adjust for this determined error. Adjusting the exhalation flow sensor 111a or other sensors for error improves the patient-ventilator synchrony.

The pneumatic system 102 may include a variety of other components, including mixing modules, valves, tubing, accumulators 124, filters, etc. For example, FIG. 1B illustrates the use of an accumulator 124.

In one embodiment, the operator interface 120 of the ventilator 100 includes a display 122 communicatively coupled to the ventilator 100. The display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, the operator interface 120 may accept commands and input through the display 122.

The display 122 may also provide useful information in the form of various ventilatory data regarding the physical condition of the patient 150. The useful information may be derived by the ventilator 100, based on data collected by the processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. In some embodiments, the display 122 may illustrate the use of an EBUV mode and/or any other information known, received, or stored by the ventilator 100, such as the estimated exhalation flow, the net flow utilizing estimated exhalation flow, estimated exhalation tidal volume, the predetermined flow deviation trigger threshold, a display representative of the time left before expiration of the predetermined amount of time, and/or other parameters determined based on estimated exhalation flow.

Figure 2:
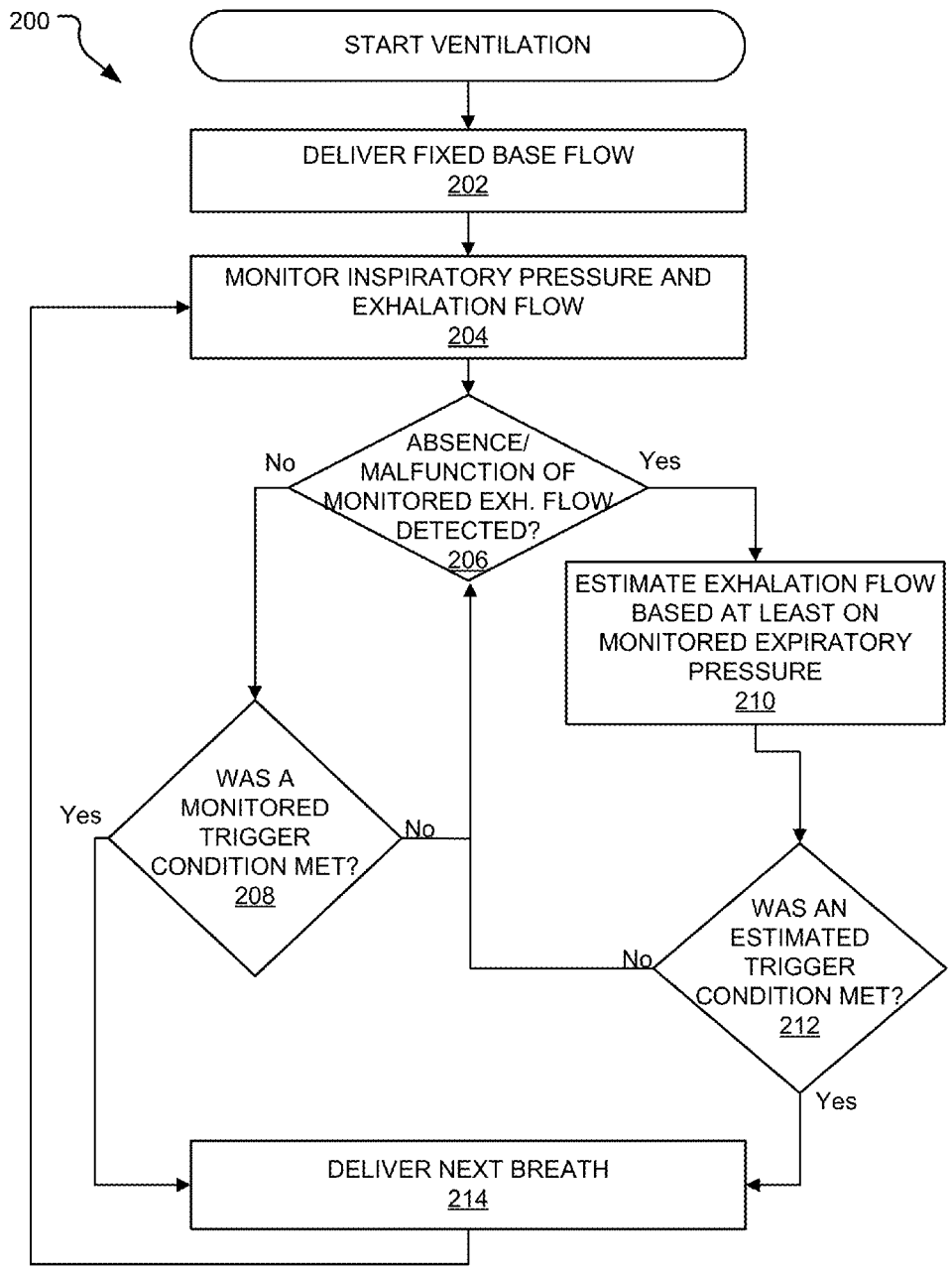
FIG. 2 illustrates an embodiment of a method for triggering inspiration during ventilation of a patient on a ventilator.

FIG. 2 illustrates an embodiment of a method 200 for triggering inspiration during ventilation of a patient on a ventilator. Further, the method 200 provides ventilation after a malfunction in the exhalation flow sensor or a removal of the exhalation flow sensor is detected that prevents the exhalation flow from being determined and/or reliable. The ventilation provided after the exhalation flow is undeterminable is referred to herein as an exhalation backup-ventilation mode (EBUV). The method 200 begins at the start of ventilation.

As illustrated, the method 200 includes a fixed base flow delivery operation 202. During the fixed base flow delivery operation 202, the ventilator delivers a fixed base flow. The fixed base flow is a continuous flow of gas through the ventilation tubing system from the inspiratory limb through the exhalation limb. This continuous flow allows the ventilator to trigger inspiration as well as determine the phase of breath (i.e. inhalation, exhalation, or between breaths) the patient is currently in. For example, if the flow through the exhalation limb is equal and opposite of the flow through the inspiratory limb, then the ventilator determines that the patient is currently between breaths as there is no flow into or out of the lungs of the patient. In a further example, if the flow through the inspiratory limb exceeds the flow through the exhalation limb, then the ventilator determines that the patient is inhaling and the flow of gas is going into the patient's lungs. In yet a further example, if the flow through the exhalation limb exceeds the flow through the inspiratory limb, then the ventilator determines that the patient is exhaling and the flow of gas is flowing from the patient's lungs (and inspiratory limb) through the exhalation limb.

Further, the method 200 includes a monitoring operation 204. During the monitoring operation 204, the ventilator monitors ventilator parameters. In some embodiments, the ventilator during the monitoring operation 204 monitors numerous ventilator parameters. As used herein ventilator parameters include any parameter that may be monitored by the ventilator. In an embodiment, the ventilator during the monitoring operation 204 monitors inspiratory flow, inspiratory pressure, exhalation flow, exhalation pressure, and/or auxiliary pressure. Sensors suitable for this detection may include any suitable sensing device as known by a person of skill in the art for a ventilator, such as an inspiratory flow sensor, inspiratory pressure sensor, an exhalation flow sensor, an exhalation pressure sensor, and/or exhalation auxiliary pressure sensor. In an embodiment, the ventilator during the monitoring operation 204 delivers ventilation based at least on the monitored exhalation flow.

The method 200 further includes a malfunction decision operation 206. During the malfunction decision operation 206, the ventilator determines if the exhalation flow is undeterminable. The ventilator during the malfunction decision operation 206 determines that the exhalation flow is undeterminable if the exhalation flow sensor is removed or if the exhalation flow sensor is malfunctioning.

Several different systems and methods are currently utilized and known in the art for determining a malfunction or a removal of an exhalation flow sensor. The ventilator during the malfunction decision operation 206 detects a malfunction or a removal utilizing any of these known systems or methods. For example, malfunctions or a removal may be detected based on changes in voltages, temperatures, wattages, coefficients, humidity, and/or overcurrent for the exhalation flow sensor. In an embodiment, during the malfunction decision operation 206, if the ventilator determines a malfunction or a removal, the ventilator displays information relating to the malfunction, the removal, or the EBUV mode such as, but not limited to, an indicator that displays the use of an EBUV mode, an estimated exhalation flow value, a flow deviation, a flow deviation trigger threshold, a trigger threshold, a predetermined amount of time used as a trigger threshold, estimated exhalation tidal volume, other estimated parameters determined utilizing the estimated exhalation flow, an indicator or notification that the exhalation flow sensor has been removed, and/or an indicator or notification of the presence of a malfunction in the exhalation flow sensor.

If the ventilator during the malfunction decision operation 206 determines that the exhalation flow is undeterminable, the ventilator selects to perform an estimation operation 210. If the ventilator during the malfunction decision operation 206 is able to determine the exhalation flow, the ventilator selects to perform a monitored trigger detection operation 208.

The method 200 includes a monitored trigger detection operation 208. The ventilator during the monitored trigger detection operation 208 determines if a first inspiratory trigger is detected. The first inspiratory trigger is detected when a monitored patient and/or ventilator parameter exceeds, or breaches, an inspiratory trigger threshold. In some embodiments, the inspiratory trigger threshold is received from operator input. In other embodiments, the inspiratory trigger threshold is based on ventilator and/or patient parameters. In some embodiments, a net negative change in flow rate below a delivered base flow is the inspiratory trigger threshold. For example, the inspiratory trigger threshold may be a change in flow rate of −1.5 LPM, −2 LPM, −3 LPM, −4 LPM, −5 LPM, −6 LPM, −7 LPM, and −8 LPM or may be a range of a change in flow rate, such as a range of −3 LPM to −6 LPM or −4 LPM to −7 LPM. This list is exemplary only and is not meant to be limiting. Any suitable change in flow rate below the delivered base flow may be utilized by the ventilator as the inspiratory trigger threshold during the monitored trigger detection operation 208. In an embodiment, a known fixed base flow and a monitored exhalation flow are combined, such as arithmetically, to determine a first net flow, or first flow deviation, that is compared against the inspiratory trigger threshold. A slight drop in the base flow through the exhalation module during exhalation may indicate that a patient is attempting to inspire. A drop in base flow is attributable to a redirection of gases into the patient's lungs (in response to a slightly negative pressure gradient).

In another embodiment, the first trigger condition is met when the patient reaches a stable portion of exhalation as determined by the ventilator during the monitored trigger detection operation 208. In order to determine a stable portion of exhalation the ventilator monitors exhalation flow and/or exhalation pressure. In some embodiments, the ventilator during the monitored trigger detection operation 208 collects multiple exhalation flow and/or exhalation pressure readings for a set period during exhalation after the expiration of a restricted period. The restricted period as used herein is a predetermined time period that starts at the beginning of exhalation. The patient is prevented from triggering ventilation during the predetermined time period of the restricted period. For example, the restricted period may be 25 ms, 50 ms, 100 ms, 200 ms, and/or any other suitable time period for preventing the patient from triggering inspiration. In an embodiment, the ventilator during the monitored trigger detection operation 208 determines stability by monitoring the exhalation flow every computation cycle. In some embodiments, the computational cycle is every 5 ms. If the difference between two successive exhalation flow readings is zero, or near zero, then a stable portion of exhalation has been determined and the ventilator selects to perform a delivery operation 214.

In an embodiment, if the ventilator during the monitored trigger detection operation 208 determines that ventilator and/or patient parameters meet and/or exceed the inspiratory trigger threshold, or first trigger condition, during exhalation, the ventilator selects to perform a delivery operation 214. If the ventilator during the monitored trigger detection operation 208 determines that ventilator and/or patient parameters do not meet and/or exceed the inspiratory trigger threshold during exhalation, or the first trigger condition, the ventilator performs malfunction decision operation 206 again.

In one embodiment, the ventilator is preconfigured to select to perform a delivery operation 214 after a predetermined amount of exhalation time to prevent the patient from becoming under-ventilated. Accordingly, the predetermined amount of exhalation time (e.g., known as an apnea interval in some ventilators) is the trigger threshold, or the first trigger condition, in this embodiment. For example, the ventilator during the monitored trigger detection operation 208 will automatically select to perform a delivery operation 214 after 20 seconds, 30 seconds, or 60 seconds of exhalation time. In some embodiments, the predetermined amount of time may be input by the clinician or calculated by the ventilator. In some embodiments, the predetermined amount of time is determined by the clinician and/or ventilator based on whether the patient is an infant, child, adult, male, female, and/or suffering from a specific disease state.

The method 200 includes the estimation operation 210. The ventilator during the estimation operation 210 determines an estimated exhalation flow or updates a previously calculated estimated exhalation flow with a more current estimated exhalation flow. The exhalation flow is estimated because the ventilator is not able to determine a reliable exhalation flow if the exhalation flow sensor is malfunctioning or removed. For example, the ventilator cannot determine the exhalation flow during EBUV. In an embodiment, the ventilator during the estimation operation 210 ceases providing ventilation based on the monitored exhalation flow and instead provides ventilation based at least on the estimated exhalation flow. Once the estimated exhalation flow is determined, the ventilator selects to perform an estimated trigger detection operation 212.

The ventilator during estimation operation 210 determines the estimated exhalation flow based on the monitored exhalation pressure and/or exhalation auxiliary pressure. In some embodiments, the ventilator during estimation operation 210 determines the estimated exhalation flow utilizing Equation #2. In order to utilize Equation #2, the ventilator during estimation operation 210 determines the constant flow coefficients during a calibration test while the exhalation flow is determinable utilizing Equation #1. Once the constant coefficients are determined for a patient, the determined constant coefficients are stored by the ventilator for use by the estimation operation 210.

In some embodiments, the ventilator during estimation operation 210 determines additional parameters utilizing the estimated exhalation flow. Parameters that are determined utilizing the estimated exhalation flow are referred to herein as estimated parameters. For example, the estimated exhalation flow may be utilized by the ventilator during estimation operation 210 to determine an estimated exhalation tidal volume.

The method 200 includes the estimated trigger detection operation 212. The ventilator during the estimated trigger detection operation 212 determines if a second inspiratory trigger is detected. The second inspiratory trigger is detected when an estimated patient and/or ventilator parameter exceeds, or breaches, an inspiratory trigger threshold. In some embodiments, the inspiratory trigger threshold is received from operator input. In other embodiments, the inspiratory trigger threshold is based on ventilator and/or patient parameters. In some embodiments, a net negative change in flow rate below a delivered base flow is the inspiratory trigger threshold. For example, the inspiratory trigger threshold may be a change in flow rate of −1.5 LPM, −2 LPM, −3 LPM, −4 LPM, −5 LPM, −6 LPM, −7 LPM, and −8 LPM or may be a range of a change in flow rate, such as a range of −3 LPM to −6 LPM or −4 LPM to −7 LPM. This list is exemplary only and is not meant to be limiting. Any suitable change in flow rate below the delivered base flow may be utilized by the ventilator as the inspiratory trigger threshold during the estimated trigger detection operation 212. Because the monitored exhalation flow is undeterminable or unreliable, the estimated exhalation flow is combined with a known fixed base flow, such as arithmetically, to determine a second net flow, or second flow deviation, that is compared against the inspiratory trigger threshold. A slight drop in the base flow through the exhalation module during exhalation may indicate that a patient is attempting to inspire. A drop in base flow is attributable to a redirection of gases into the patient's lungs (in response to a slightly negative pressure gradient).

In another embodiment, the second trigger condition is met when the patient reaches a stable portion of exhalation as determined by the ventilator during the estimated trigger detection operation 212. In order to determine a stable portion of exhalation the ventilator during the estimated trigger detection operation 212 monitors the estimated exhalation flow. In some embodiments, the ventilator during the estimated trigger detection operation 212 collects multiple exhalation flow estimates for a set period during exhalation after the expiration of a restricted period. The restricted period as used herein is a predetermined time period that starts at the beginning of exhalation. The patient is prevented from triggering ventilation during the predetermined time period of the restricted period. For example, the restricted period may be 25 ms, 50 ms, 100 ms, 200 ms, and/or any other suitable time period for preventing the patient from triggering inspiration. In an embodiment, the ventilator during the estimated trigger detection operation 212 determines stability by monitoring the estimated exhalation flow every computation cycle. In some embodiments, the computational cycle is every 5 ms. If the difference between two successive exhalation flow estimates is zero, or near zero, then a stable portion of exhalation has been determined and the ventilator selects to perform a delivery operation 214.

In an embodiment, if the ventilator during the estimated trigger detection operation 212 determines that ventilator and/or patient parameters meet and/or exceed the inspiratory trigger threshold during exhalation, or the second trigger condition, the ventilator selects to perform a delivery operation 214. If the ventilator during the estimated trigger detection operation 212 determines that ventilator and/or patient parameters do not meet and/or exceed the inspiratory trigger threshold during exhalation, or the second trigger condition, the ventilator performs malfunction decision operation 206 again.

In one embodiment, the ventilator is preconfigured to select to perform a delivery operation 214 after a predetermined amount of exhalation time to prevent the patient from becoming under-ventilated. Accordingly, the predetermined amount of exhalation time is the trigger threshold, or second trigger condition, in this embodiment. For example, the ventilator during the estimated trigger detection operation 212 will automatically select to perform a delivery operation 214 after 20 seconds, 30 seconds, or 60 seconds of exhalation time. In some embodiments, the predetermined amount of time may be input by the clinician or calculated by the ventilator. In some embodiments, the predetermined amount of time is determined by the clinician and/or ventilator based on whether the patient is an infant, child, adult, male, female, and/or suffering from a specific disease state.

Further, the method 200 includes the delivery operation 214. The ventilator during the delivery operation 214 delivers a next breath to the patient. The breath delivered to the patient may be determined by the ventilator and/or patient parameters. For example, the delivered breath may be based on a selected breath type or ventilation mode, such as EBUV. After the breath is delivered to the patient, the ventilator selects to return to the monitoring operation 204.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known.

Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the claims.

What is claimed is:

1. A method for ventilating a patient with a ventilator, comprising:
    delivering a fixed base flow;
    monitoring an exhalation flow, an exhalation pressure, and an exhalation auxiliary pressure during ventilation of the patient with the fixed base flow based on output from one or more sensors to determine a monitored exhalation flow, a monitored exhalation pressure, and a monitored exhalation auxiliary pressure;
    detecting a first trigger condition based at least on the monitored exhalation flow;
    triggering inspiration in response to the detecting of the first trigger condition;
    determining an absence of the monitored exhalation flow with the ventilator based on the output from the one or more sensors; and the ventilator in response to the determining:
        ceasing to utilize the first trigger condition based at least on the exhalation flow;
        estimating the exhalation flow based on the monitored exhalation pressure and the monitored exhalation auxiliary pressure to determine an estimated exhalation flow;
        detecting a second trigger condition based at least on the estimated exhalation flow; and
        triggering inspiration during the ventilation in response to the detecting of the second trigger condition.

2. The method of claim 1, wherein the second trigger condition is detection of a stable portion of exhalation flow at about zero.

3. The method of claim 1, wherein the second trigger condition is a negative change in base flow after a stable portion of exhalation is reached decreases below zero.

4. The method of claim 1, wherein the second trigger condition is a flow deviation based on the fixed base flow and the estimated exhalation flow that breaches a trigger threshold.

5. The method of claim 4, wherein the trigger threshold is a drop in the estimated exhalation flow of at least 1.5 LPM.

6. The method of claim 4, wherein the trigger threshold is a range of a change in flow of −0.1 LPM to −20 LPM.

7. The method of claim 1, further comprising:
    monitoring an exhalation time during the ventilation of the patient with the ventilator;
    detecting a third trigger condition based at least on a monitored exhalation time; and triggering inspiration in response to the detecting of the third trigger condition.

8. The method of claim 7, wherein the third trigger condition is the exhalation time of at least 20 seconds.

9. The method of claim 1, wherein the absence of the monitored exhalation flow is because an exhalation flow sensor is removed from the ventilator.

10. The method of claim 1, wherein the absence of the monitored exhalation flow is because of a malfunction in an exhalation flow sensor.

11. The method of claim 1, further comprising:
determining an estimated exhaled tidal volume based at least on the estimated exhalation flow in response to the detecting of the absence of the monitored exhalation flow; and
displaying the estimated exhaled tidal volume.

12. The method of claim 1, further comprising:
in response to the absence of the monitored exhalation flow:
displaying at least one of a notification that an exhalation flow sensor is removed, a notification that the exhalation flow sensor is malfunctioning, the estimated exhalation flow, and the second trigger condition.

13. A ventilator system comprising:
a pressure generating system that generates a flow of breathing gas including a fixed base flow;
a ventilation tubing system including a patient interface for connecting the pressure generating system to a patient;
an exhalation valve connected to the ventilation tubing system;
a plurality of sensors operatively coupled to at least one of the pressure generating system, the patient, and the ventilation tubing system for monitoring inspiratory pressure, inspiratory flow, exhalation pressure, exhalation auxiliary pressure, and exhalation flow to determine a monitored inspiratory pressure, a monitored inspiratory flow, a monitored exhalation pressure, a monitored exhalation auxiliary pressure, and a monitored exhalation flow;
an exhalation flow estimation module, the exhalation flow estimation module estimates the exhalation flow based on the monitored exhalation pressure and the monitored exhalation auxiliary pressure to determine an estimated exhalation flow;
a driver, the driver controls the exhalation valve to deliver ventilation to the patient based at least on at least one of the monitored exhalation flow, and the estimated exhalation flow determined based on the monitored exhalation pressure and the monitored exhalation auxiliary pressure;
a main trigger module, the main trigger module triggers an inspiration based on a first of at least one of the following events to occur:
detection of a first trigger condition based at least on the monitored exhalation flow, and
expiration of a predetermined amount of exhalation time;
a backup trigger module, the backup trigger module triggers the inspiration based on a first of at least one of the following events to occur:
detection of a second trigger condition based at least on the estimated exhalation flow, and
expiration of the predetermined amount of exhalation time;
a controller, the controller determines an absence in the monitored exhalation flow and switches from the main trigger module to the backup trigger module.

14. The ventilator system of claim 13, further comprising:
a display that displays at least one of a notification that an exhalation flow sensor is removed, a notification that the exhalation flow sensor is malfunctioning, the estimated exhalation flow, and the second trigger condition.

15. The ventilator system of claim 13, wherein the controller detects the absence of the monitored exhalation flow because an exhalation flow sensor has been removed.

16. The ventilator system of claim 13, wherein the controller detects the absence of the monitored exhalation flow because an exhalation flow sensor is malfunctioning.

17. The ventilator system of claim 13, further comprising:
a display that displays the estimated exhalation flow and an estimated exhalation tidal volume, wherein the exhalation flow estimation module estimates an exhalation tidal volume based on the estimated exhalation flow.

18. The ventilator system of claim 13, wherein the second trigger condition is detection of a stable portion of exhalation.

19. The ventilator system of claim 13, wherein the second trigger condition is a flow deviation based on the fixed base flow and the estimated exhalation flow that breaches a trigger threshold.

20. A method for ventilating a patient with a ventilator, comprising:
monitoring an exhalation flow, an exhalation pressure, and an exhalation auxiliary pressure during ventilation of the patient with the ventilator based on output from one or more sensors to determine a monitored exhalation flow, a monitored exhalation pressure, and a monitored exhalation auxiliary pressure;
delivering ventilation based at least on the monitored exhalation flow;
determining an absence in the monitored exhalation flow with the ventilator based on the output from the one or more sensors;
in response to the absence of the monitored exhalation flow, estimating the exhalation flow based at least on the monitored exhalation pressure and exhalation auxiliary pressure to determine an estimated exhalation flow; and
in response to the absence of the monitored exhalation flow, ceasing to deliver the ventilation based at least on the monitored exhalation flow and instead delivering ventilation based at least on the estimated exhalation flow.

* * * * *